US012708544B2

(12) United States Patent
Mcdaid et al.

(10) Patent No.: US 12,708,544 B2
(45) Date of Patent: Aug. 18, 2026

(54) ORTHOSIS OR EXOSKELETON SYSTEM WITH MODULAR ELEMENTS

(71) Applicant: OPUM TECHNOLOGIES LIMITED, Hamilton (NZ)

(72) Inventors: Andrew John Mcdaid, Hamilton (NZ); William Edwin John Grant, Hamilton (NZ)

(73) Assignee: OPUM TECHNOLOGIES LIMITED, Hamilton (NZ)

( * ) Notice: Subject to any disclaimer, the term of this patent is extended or adjusted under 35 U.S.C. 154(b) by 331 days.

(21) Appl. No.: 18/615,137

(22) Filed: Mar. 25, 2024

(65) Prior Publication Data

US 2024/0225879 A1 Jul. 11, 2024

Related U.S. Application Data

(63) Continuation of application No. 16/624,690, filed as application No. PCT/NZ2018/050085 on Jun. 20, 2018, now abandoned.

(30) Foreign Application Priority Data

Jun. 20, 2017 (NZ) ........................................ 732984

(51) Int. Cl.
*A61H 1/02* (2006.01)
*A61F 5/01* (2006.01)
(Continued)

(52) U.S. Cl.
CPC ............ *A61F 5/0125* (2013.01); *A61F 5/013* (2013.01); *A61F 5/042* (2013.01); *A61H 1/024* (2013.01);
(Continued)

(58) Field of Classification Search
CPC ..... A61F 5/0123; A61F 5/0125; A61H 1/024; A61H 3/00; A61H 2201/165; A61H 2201/5069
See application file for complete search history.

(56) References Cited

U.S. PATENT DOCUMENTS 4,776,326 A * 10/1988 Young .................. A61F 5/0102
602/26
5,052,379 A 10/1991 Airy et al.
(Continued)

FOREIGN PATENT DOCUMENTS

DE 102015217205 3/2017
WO 2004/078078 9/2004
(Continued)

OTHER PUBLICATIONS

English translation of Moreno et al. (WO 2018178427 A1) (Year: 2018).*
(Continued)

*Primary Examiner* — Timothy A Stanis
*Assistant Examiner* — Christopher E Miller
(74) *Attorney, Agent, or Firm* — Leason Ellis LLP

(57) ABSTRACT

There is provided an orthosis or exoskeleton system (200) comprising: one or more body mounting modules (102), the or each body mounting module being structured and arranged to, in use, be mounted to one or more parts of a body of a patient, the body mounting modules having different sizes or configurations with respect to each other; and one or more function modules (104), the or each function module being structured and arranged to provide a different sensing, charging or control function; the body mounting modules and the function modules each having an
(Continued)

interfacing structure such that any said body mounting module is interchangeably couplable to any said function module.

13 Claims, 21 Drawing Sheets

(51) Int. Cl.
*A61F 5/042* (2006.01)
*A61H 3/00* (2006.01)
(52) U.S. Cl.
CPC ............. *A61H 1/0277* (2013.01); *A61H 3/00* (2013.01); *A61F 2005/0155* (2013.01); *A61H 2201/0107* (2013.01); *A61H 2201/165* (2013.01); *A61H 2201/1676* (2013.01); *A61H 2201/1685* (2013.01); *A61H 2201/5023* (2013.01); *A61H 2201/5061* (2013.01); *A61H 2201/5069* (2013.01); *A61H 2201/5079* (2013.01); *A61H 2201/5084* (2013.01); *A61H 2201/5097* (2013.01); *A61H 2205/06* (2013.01); *A61H 2205/102* (2013.01)

(56) References Cited

U.S. PATENT DOCUMENTS

| | | | | |
|---|---|---|---|---|
| 5,344,390 | A | 9/1994 | Motloch | |
| 5,662,594 | A | 9/1997 | Rosenblatt | |
| 6,517,503 | B1 | 2/2003 | Naft et al. | |
| 6,656,144 | B1 * | 12/2003 | Coligado | A61F 5/0125 602/26 |
| 7,150,721 | B2 | 12/2006 | Houser | |
| 7,235,059 | B2 | 6/2007 | Mason et al. | |
| 7,462,160 | B2 | 12/2008 | Nobbe et al. | |
| 8,172,781 | B2 | 5/2012 | Oddou et al. | |
| 8,939,924 | B1 * | 1/2015 | Paulos | A61F 5/01 602/5 |
| 10,617,549 | B2 | 4/2020 | Frost et al. | |
| 2006/0200057 | A1 | 9/2006 | Sterling | |
| 2007/0010772 | A1 * | 1/2007 | Ryan | A61F 5/0123 602/26 |
| 2008/0234608 | A1 | 9/2008 | Sankai | |
| 2009/0030356 | A1 | 1/2009 | Maloney | |
| 2010/0113980 | A1 * | 5/2010 | Herr | G01L 5/0028 600/587 |
| 2010/0130898 | A1 * | 5/2010 | Franke | A61F 5/0195 602/23 |
| 2010/0298746 | A1 * | 11/2010 | Shimizu | B25J 9/0006 601/35 |
| 2011/0136376 | A1 | 6/2011 | Johnson et al. | |
| 2011/0306911 | A1 * | 12/2011 | Tran | A61F 5/0125 602/16 |
| 2011/0313331 | A1 * | 12/2011 | Dehez | A61H 1/0285 601/33 |
| 2012/0046584 | A1 | 2/2012 | Maloney | |
| 2012/0259259 | A1 | 10/2012 | Chugunov | |
| 2013/0253396 | A1 * | 9/2013 | Chetlapalli | A61F 5/0125 602/16 |
| 2014/0039367 | A1 * | 2/2014 | Boraas | A61F 5/01 602/7 |
| 2014/0240109 | A1 | 8/2014 | Aviles et al. | |
| 2015/0051527 | A1 | 2/2015 | Potter et al. | |
| 2016/0213924 | A1 * | 7/2016 | Coleman | A61N 1/0484 |
| 2018/0104075 | A1 * | 4/2018 | Mooney | B25J 9/0006 |

FOREIGN PATENT DOCUMENTS

| | | |
|---|---|---|
| WO | 2010/088716 | 8/2010 |
| WO | 2014/151584 | 9/2014 |
| WO | 2016/136355 | 9/2016 |
| WO | 2016/146960 | 9/2016 |

OTHER PUBLICATIONS

International Search Report and Written Opinion in corresponding PCT Application No. PCT/NZ2018/050085, mailed Nov. 1, 2018.
Final Office Action in U.S. Appl. No. 16/624,690, mailed Oct. 25, 2023 (41 pages).
Non-Final Office Action in U.S. Appl. No. 16/624,690, mailed Jan. 27, 2023 (36 pages).

* cited by examiner

ORTHOSIS OR EXOSKELETON SYSTEM WITH MODULAR ELEMENTS

CROSS-REFERENCE TO RELATED PATENT APPLICATIONS

This application is a continuation of U.S. application Ser. No. 16/624,690, filed Dec. 19, 2019, which is a U.S. National Phase Application under 35 U.S.C. § 371 of International Patent Application No. PCT/NZ2018/050085, filed Jun. 20, 2018, which claims the priority of NZ Patent Application 732984, filed Jun. 20, 2017, each of which is incorporated by reference as if expressly set forth in their respective entirety herein.

FIELD OF INVENTION

The present invention is directed to a patient attachment system such as an orthosis, exoskeleton or rehabilitation robot and comprising modular elements for use in the rehabilitation, support, monitoring, diagnosis or prevention of afflictions and/or injuries of a human or animal patient, neuromuscular, skeletal and/or otherwise.

BACKGROUND TO THE INVENTION

Individuals suffering from injury and disease commonly require a range of rehabilitative strategies with the objective of recovering to maximise their ability and reducing time to reach that maximum ability. Individuals may additionally or separately need assistance to compensate for any lost function. Additionally healthy individuals may wish to improve their abilities beyond their current capability and or enhance function. In one or all of these cases an individual may want to assess or diagnose their current ability and compare it to historic and/or future states.

Robotic and sensorised devices such as orthosis systems (orthotics) or exoskeletons may be useful in a number of fields including rehabilitation, assessment, assistance, performance improvement, but show particular promise in the field of rehabilitation, for example for ACL injuries or stroke victims. Such devices are typically configured to be used for a specific application, for a specific person's physical size and body part, for example a large knee brace for ACL rehabilitation.

At an early (acute) impairment stage a human has a different ability and hence different requirements than in the later (chronic) stages.

Throughout a day a patient performs different tasks which require different levels of assistance. For example during the day no assistance may be needed but at night when performing rehabilitative exercises a resistance torque may be required to be applied to the joint. A patient may typically have different rehabilitative needs at different stages of injury and recovery, which require different systems and methods of treatment at various times. A patient may typically require varying therapy and assistance plans throughout the recovery process. An individual may also require rehabilitation on a multitude of joints, sequentially or concurrently. A clinic, hospital and/or clinician may typically have more than one of patients that have different and changing requirements with time, including different joints and limbs as well as be different sizes.

A number of problems or challenges exist with the systems and methods of rehabilitation of the prior art.

One problem is that the human attachment components of the systems of the prior art are directly and permanently coupled to the functional components of the system meaning that a separate system is needed for every different function for a particular patient.

A second problem is that the wearable apparatuses are expensive, complex and time consuming to customise.

A further problem is the need to adapt a rehabilitative system as the patient progresses through their plan (from injury to recovery).

A further problem is the need for a clinician to use a rehabilitative system on multiple patients with various requirements without requiring to have in stock multiple numbers of every combination of systems so they can treat more than one patient with the same requirements.

A further challenge is the need for an efficient method of delivery of rehabilitation in remote and/or rural settings where systems are necessarily prescribed and/or delivered to patients to affect rehabilitation without the need of a trained clinician to physically visit the patient to update the system.

A further challenge is the need to keep the weight and bulk of a powered system to a minimum. A further problem is the need to continuously collect data from a patient throughout a given day and when performing different activities (such as rehabilitation exercises) and throughout the entire recovery from injury and disease.

A further challenge is the ability to accurately diagnose and predict outcomes (such as recovery time and extent) following injury and disease to provide planning tools for a person to return to employment duties, sport, a mission or military service.

A further challenge is the ability to predict and hence plan optimal treatment regimes, including surgical and/or pharmacological interventions such as Botox injections.

A further challenge is the ability to compare a specific person's rehabilitation progress to a larger population of individuals to understand their performance relative to the "normal" trajectory of rehabilitation in terms of time and extent of recovery.

OBJECT OF THE INVENTION

It is an object of the invention to provide a system, device and/or method for performing any one or more of rehabilitation, assistance and diagnosis to overcome or ameliorate problems with existing systems and methods. Alternatively, it is an object to provide an improved orthosis system. Alternatively, it is an object of the invention to at least provide the public with a useful choice.

SUMMARY OF THE INVENTION

Aspects of the present invention are directed towards providing medical devices used in the rehabilitation, support, monitoring, diagnosis or prevention of neuromuscular and/or skeletal afflictions having one or more of improved ease of use, customisability and efficacy.

One aspect of the present invention is an orthosis or exoskeleton system. Another aspect is a sensing/control module for use in an orthosis or exoskeleton system. Another aspect is a pad for use in an orthoses or exoskeleton system.

One aspect of the invention is an orthosis or exoskeleton system comprising modular elements. The modular elements may be configured for use in the rehabilitation, support, monitoring, diagnosis or prevention of neuromuscular and/or skeletal afflictions of a patient. For example, the modular elements may be configured to monitor the patient, monitor the orthosis or exoskeleton system, control the orthosis or exoskeleton system, and/or support the or exoskeleton orthosis system on the patient.

In one aspect there is provided an orthosis or exoskeleton system comprising:

- one or more body mounting modules, the or each body mounting module being structured and arranged to, in use, be mounted to one or more parts of a body of a patient, the body mounting modules having different sizes or configurations with respect to each other; and
- one or more function modules, the or each function module being structured and arranged to provide a different sensing, charging or control function;
- the body mounting modules and the function modules each having an interfacing structure such that any said body mounting module is interchangeably couplable to any said function module.

The system may comprise a plurality of body mounting modules and one or more function modules, a plurality of function modules and one or more body mounting modules, or a plurality of both. The common interfacing structures on the body mounting module and on the function modules are complimentary to each other such that any function module and removably and interchangeably couple to a body mounting module.

The interfacing structures are configured to provide a quick release or tool-less coupling between respective body mounting modules and function modules. This allows fast one-handed operation by a patient or clinician.

A body mounting module may be structured and arranged to be mounted to a first and a second body part of a patient, the first and second body part being on either side of a joint; for example a knee or elbow.

A function module, also referred to herein as a sensing/control module, may be configured to provide one or more of the following: a sensing function; an energy function; an actuation or control function. The sensing function may be dependent on an angle between the first and second body part. The energy function may be an energy generation and/or storage and/or charging function, for example energy may be harvested from the joint itself. The actuation function may be resistance or enhancement of joint movements.

The body mounting modules and the function modules may have corresponding transfer interfaces such that information or action may be transferred between a said body mounting module and a said function module when coupled. The information or action is transferred over the transfer interface using a mechanism selected from one of the following: mechanical; electrical; optical; magnetic; electromagnetic.

The information may be selected from one of the following: an angle between different parts of the body mounting module; an orientation of the body mounting module or function module; movement of the body mounting module or function module; muscle activity of a body part of the patient; patient proximity; body temperature; heart rate; respiration rate; blood pressure; blood oxygen level; joint/body forces and/or load (for example due to gravity, movement and/or interaction between the device and the body of the patient); other physiological parameters.

The action is selection from one of the following: resistance or dampening of movement between different parts of the body mounting module; electrical power flow for charging; electrical stimulation of muscles of a body part of the patient; actuation of movement between different parts of the body; heating or cooling of a body part; massage the body of a patient; mechanical perturbation to check joint laxity, muscle or joint stiffness and tone.

In an embodiment the body mounting module comprises first and second brace assemblies, the second brace assembly moveably coupled to the first brace assembly. Various hinging arrangements are possible including unicentric and polycentric, as well as 4-bar linkage.

The first and second brace assemblies each comprise first and second brace interfacing structures respectively forming a said interfacing structure of the body mounting module, the interfacing structure of the functional module being complimentary and arranged to engage with the first and second brace interfacing structures when the functional module is coupled to the body mounting module.

The first and second brace assemblies may each comprise first and second pivot portions respectively, the first and second pivot portions being pivotably coupled at a pivot assembly, the pivot assembly being configured to couple to the functional module.

The pivot assembly may be configured to couple to the functional modules by rotating the functional modules relative to the pivot assembly.

The function module interfacing structure and the first brace interfacing structure may comprise a first locking mechanism to lock the orientation of the second brace assembly relative to the first brace assembly.

The functional module may comprise a rotation limitation mechanism configured to limit rotation of the first brace assembly relative to the second brace assembly.

The functional module may comprise a resistance mechanism configured to provide a predetermined level of resistance to rotation of the first brace assembly relative to the second brace assembly.

In an alternative embodiment, the first brace assembly may be pivotably coupled to the second brace assembly using a polycentric hinge.

The first and second brace assemblies may each comprise a pivot point at a distal end and gear teeth at said distal end, the gear teeth of the first and second brace assemblies arranged to engage such that the first and second brace assemblies rotate about their respective pivot points by the same angle but in opposite directions.

The transfer interface of body mounting module comprises a magnet which is arranged to rotate with the first brace assembly, and the transfer interface of the function module comprises a sensor arranged to detect the rotation of the magnet.

The interfacing structure of the body mounting module comprises a slide-able lock mechanism and the interfacing structure of the function module comprises a locking recess which is arranged to engage with the slide-able hook mechanism to couple the body mounting module to the function module. The interfacing structure of the body mounting module may also comprise a number of locating recesses and the interfacing structure of the function module may also comprise a number of locating projections which are arranged to engage with the locating recesses to couple the body mounting module to the function module There is also provided a body mounting module of an orthosis or exoskeleton system having a number of function modules structured and arranged to provide a sensing, energy and/or control functions and having an interfacing structure for coupling with the body mounting module; the body mounting module being structured and arranged to, in use, be mounted to one or more parts of a body of a patient; the body mounting module having an interfacing structure comprising one or more of the following:

- a slide-able lock mechanism for engaging with a locking recess of a said function module, and a number of locating recesses for engaging with corresponding locating projections of the function module;

first and second brace interfacing structures respectively forming a said interfacing structure of the body mounting module, and which may comprise first and second pivot portions respectively, the first and second pivot portions being pivotably coupled at a pivot assembly, the pivot assembly being configured to couple to the functional module, the pivot assembly may be configured to couple to the functional modules by rotating the functional modules relative to the pivot assembly.

There is also provided a function module of an orthosis or exoskeleton system having a number of body mounting modules structured and arranged to be mounted to one or more parts of a body of a patient and having an interfacing structure for coupling with the body mounting module; the function module being structured and arranged to, in use, to provide a sensing, energy and/or control function; the function module having an interfacing structure comprising one or more of the following:

a locking recess for engaging with a slide-able lock mechanism of a said body mounting module, and a number of locating projections for engaging with corresponding locating recesses of the function module;

a flange configured to couple to the body mounting module by rotating the functional module relative to the body mounting module; preferably at a pivot assembly where first and second pivot portions are pivotably coupled, the first and second pivot portions forming parts of first and second first and second brace interfacing structures respectively.

According to another aspect of the invention, there is provided an orthosis system comprising:

a body mounting module, the body attachment module being structured and arranged to, in use, be mounted to a part of a body of a patient; and a plurality of function or sensing/control modules, each of the function or sensing/control modules being configured to be removably coupled to the body mounting module, the function or sensing/control modules being different from each other in at least one aspect.

Preferably, the body mounting module comprises first and second brace assemblies, the second brace assembly moveably coupled to the first brace assembly.

Preferably, the function or sensing/control modules each comprise a module interfacing structure and the first and second brace assemblies each comprise first and second brace interfacing structures respectively, the module interfacing structure interfacing with the first and second brace interfacing structures when the sensing/control modules are coupled to the body mounting module. The sensing/control modules may interface physically, electrically and/or magnetically with the first and second brace interfacing structures.

Preferably the first brace assembly is pivotably coupled to the second brace assembly at a pivot. More preferably, the first and second brace assemblies each comprise first and second pivot portions respectively, the first and second pivot portions being pivotably coupled at a pivot assembly, the pivot assembly being configured to couple to the sensing/control modules.

Preferably, the pivot assembly is configured to couple to the sensing/control modules by rotating the sensing/control modules relative to the pivot assembly. For example, in one embodiment, the pivot assembly comprises a first flange and the module interfacing structure comprises a second flange, the first and second flanges interlocking by rotating the sensing/control modules relative to the pivot assembly. The first flange may be comprised as part of the first brace interfacing structure or the second brace interfacing structure.

More preferably the module interfacing structure and the first brace interfacing structure comprise a first locking mechanism to lock the orientation of the sensing/control modules relative to the first brace assembly. More preferably the module interfacing structure and the second brace interfacing structure comprise a second locking mechanism to lock the orientation of the sensing/control modules relative to the second brace assembly.

Preferably, a rotation sensing/control module of the sensing/control modules comprises a first module portion and a second module portion, the first and second module portions being structured and arranged to rotate relative to each other in use.

Preferably the module interfacing structure comprises a first module interfacing structure part and a second module interfacing structure part, the first and second module interfacing parts to interface with the first and second brace interfacing structures respectively, the first and second module portions comprising the first and second module interfacing parts respectively.

Preferably, the rotation sensing/control module comprises a rotation limitation mechanism configured to limit rotation of the first brace relative to the second brace. The rotation limitation mechanism may be configured to enable setting of rotation limits beyond which rotation of the first module portion relative to the second module portion is substantially prevented.

Preferably, the sensing/control module comprises a resistance mechanism configured to provide a predetermined level of resistance to rotation of the first module portion relative to the second module portion.

Preferably, the sensing/control module comprises a movement sensor configured to sense movement of the orthosis system, for example movement of the first brace assembly relative to the second brace assembly. More preferably, the rotation sensing/control module comprises a rotation sensor configured to sense rotation of the first module portion relative to the second module portion.

Preferably, the rotation sensing/control module comprises a torque sensor configured to sense torque imparted by the first module portion on the second module portion, or vice versa.

Preferably, the sensing/control module comprises an actuator configured to control movement of the orthosis system, for example movement of the first brace assembly relative to the second brace assembly. The sensing/control module may comprise a controller configured to control the actuator. The controller may be configured to receive control signals from a remote location.

In one embodiment, the rotation sensing/control module comprises a rotation actuator configured to rotate the first module portion relative to the second module portion.

Preferably, the orthosis system comprises a physiological sensor configured to sense physiological characteristics of the patient. The physiological characteristics may include, but are not limited to: body temperature; heart rate; muscle electrical activity; respiration rate; blood pressure; and blood oxygen level.

Preferably, the orthosis system comprises a use sensor configured to sense use of the orthosis system. In one embodiment the use sensor comprises a proximity sensor and/or a contact sensor on a part of the orthosis system in contact with the patient in use.

In some embodiments of the technology, the sensing/control module comprises a transmitter configured to transmit data generated by a sensor of the orthosis system to a remote location.

The sensing/control module may also comprise a receiver configured to receive data from a remote location.

Preferably the body mounting module comprises a frame and a pad coupled to the frame via a pad connector, the pad configured to contact the body in use to support the orthosis system on the body. More preferably, the body mounting module comprises a plurality of pads coupled to the frame, each pad configured to contact the patient's body in use.

Alternatively or additionally, the body mounting module may comprise a plurality of pads configured to contact the patient's body in use, each pad configured to be removably coupled to the frame, the pads being different from each other in at least one aspect. For example, the plurality of pads may be different sizes, shapes, colours and/or textures.

Preferably, the pad connector is configured to removably couple the pad to the frame.

Preferably, the pad connector is configured to adjustably couple the pad to the frame. For example, the position of the pad relative to the frame may be adjusted to accommodate different size and/or shape patients.

In one embodiment, the pad connector comprises a ratchet mechanism.

According to another aspect of the invention, there is provided an orthosis system comprising:

- a body mounting module, the body attachment module being structured and arranged to, in use, be mounted to a part of a patient's body; and
- a sensing/control module coupled to the body mounting module,
- wherein the body mounting module comprises:
  - a frame; and
  - a plurality of pads configured to contact the patient's body in use, each pad configured to be interchangeably coupled to the frame, the pads being different from each other in at least one aspect.

According to another aspect of the invention, there is provided a sensing/control module for an orthosis system according to any one or more of the aforementioned aspects of the invention.

According to another aspect of the invention, there is provided a pad for an orthosis system according to any one or more of the aforementioned aspects of the invention.

According to another aspect of the invention, there is provided a system for performing rehabilitation/improvement/assistance/diagnostics/assessment/prediction/automatic prescription for at least one joints and/or at least one limb/body segments, the system comprising:

- a modular apparatus with at least one attachment to the human body proximal and/or distal to the joint and/or at least one to a limb/body segment;
- a modular apparatus with at least one 'functional module', with at least one other function other than (excluding) to attach/couple to the human, that can (dis)connect/interchange to at least one of the 'human attachment' modules, without removing the 'human attachment' module from the human to perform specific functions;
- a modular apparatus where mechanical, electrical, magnetic, inductive/electromagnetic force/information is passed between the 'human attachment' and 'functional' modules.

Preferably, the functional modules include a mechanical range of motion limiting system to restrict joint angles.

Preferably, the functional modules include a mechanical range of motion limiting system which can be manually adjusted to restrict joint angles. Alternatively or additionally, the functional modules include a mechanical range of motion limiting system which can be automatically adjusted with an actuator and control input to restrict joint angles.

Preferably, the control input is received from a wireless device such as a computer or mobile device.

Preferably, the control input is from a wireless device and is dependent on the current or previous activity and/or state/wellbeing/capability of the wearer.

Preferably, the functional modules include a mechanical range of motion limiting system to restrict joint angles with a cushioned stop/limit using a compliant member such as a spring or elastomer.

Preferably, the functional modules include at least one of sensors for monitoring joint kinematics (angle, velocity and acceleration) and limb motion, e.g. encoders and/or IMUs (accelerometers, gyroscopes and magnetometers).

Preferably, the functional modules include at least one of sensors for monitoring joint angle and limb motion, e.g. encoders and/or IMUs (accelerometers, gyroscopes and magnetometers).

Preferably, the functional and/or human attachment modules include at least one of sensors for monitoring if the wearer has the brace on.

Preferably, the modules include at least one of sensors for monitoring joint interaction torque between the patient and human attachment module.

Preferably, the functional modules include at least one sensor for monitoring torque that uses the relative displacement between a complaint member as measured by two angular sensors and knowledge of the properties of the resilient member.

Preferably, the functional modules include at least one of sensors for monitoring joint kinematics which is then used with a computational model to calculate physiological/biomechanical properties including but not limited to muscle force, muscle length, velocity and joint torque and limb/joint loads.

Preferably, the functional modules include at least one of sensors for monitoring bio-signals such as EMG, or high-density EMG arrays.

Preferably, the functional modules include sensors for monitoring other patient physiology, e.g. temperature, humidity, heartrate, etc.

Preferably, the functional modules include at least one sensor and at least one actuator. More preferably, the functional modules include at least one actuator for transmitting power to the human to affect rehabilitation, assessment or performance improvement. Preferably, the functional modules include at least one sensor and at least one actuator for monitoring and transferring power to the human to affect rehabilitation, assessment or performance improvement. Preferably, the functional modules include at least one sensor and at least one actuator where the actuator power is transmitted via a (flexible and/or rigid) transmission such as a Bowden cable and springs for monitoring and transferring power to the human to affect rehabilitation, assessment or performance improvement. Preferably, the functional modules include a separate functional module for an actuator which is connected to an intermediate functional module for power/data transmission, which is then connected to the human attachment module.

Preferably, the functional modules contain a compliant member and/or energy dissipating mechanism such as a torsional spring or friction brake to provide a specific resistance to the joint Preferably, the functional modules contain a compliant member such as an elastomer coupling to provide a specific resistance to the joint.

Preferably, the compliant member is configured with properties to match the individual wearer's ability and rehabilitation/clinical goals.

Preferably, the properties (e.g. stiffness, damping etc) can be adjusted (e.g. screw to tighten friction).

Preferably, the property setting is chosen and set automatically using an actuator and data from an input controller/algorithm or manually using the data collected by the sensors.

Preferably, the functional modules contain a handle where the patient or other person/clinician can manipulate the joint/limb to exercise and/or collect data.

Preferably, there is a sensor to measure the displacement and torque between the user force on the handle and the wearers joint/limb.

Preferably, the sensor uses the relative displacement between a compliant member as measured by two displacement sensors to infer torque/force between the user force on the handle and the wearers joint/limb.

Preferably, at least one human attachment module is connected to at least one other human attachment module.

Preferably, at least one human attachment module has at least one modular pad for attaching to the limb.

Preferably, the pads and structural support are mass-customised for multiple patients, e.g. mass produce different sizes and customers choose their size pads and arms, etc, to customise for themselves.

Preferably, the pads are different colours and aesthetic designs and are chosen by the customer to provide customisation.

Preferably, the pads are designed directly by a patient to give their own aesthetic design via a drawing submitted by various means, including but not limited to a web or mobile app, which can then be manufactured and sent to the patient.

Preferably, in each attachment zone to the human limb of a human-attachment module, e.g. separately for the thigh and shank for a knee brace, the front and back pads are individually adjusted relative to the structural support of the orthosis.

Preferably, the adjustments use a micro-adjustment system.

Preferably, at least one functional module includes vibrotactile, neuromuscular electrical stimulation, audio or other haptic or actuation means to provide real-time feedback to the patient.

Preferably, the human attachment module contains at least one sensor. Preferably, the human attachment module contains at least one sensor and communication system to wirelessly transfer data. Preferably, the human attachment module contains at least one sensor and/or at least one actuator.

Preferably, the human attachment module contains at least one sensor and/or at least one power transmission system (to be coupled with an actuator).

Preferably, at least one functional module works together with at least one other functional module with associated human attachment modules to perform a specific task requiring at least two joints and/or at least two limb segments.

Preferably, data generated by and/or detected by the orthosis system is stored or transferred wirelessly to a remote location for assessment.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

BRIEF DESCRIPTION OF PREFERRED EMBODIMENTS OF THE INVENTION

Modular Orthosis System

Figure 1:
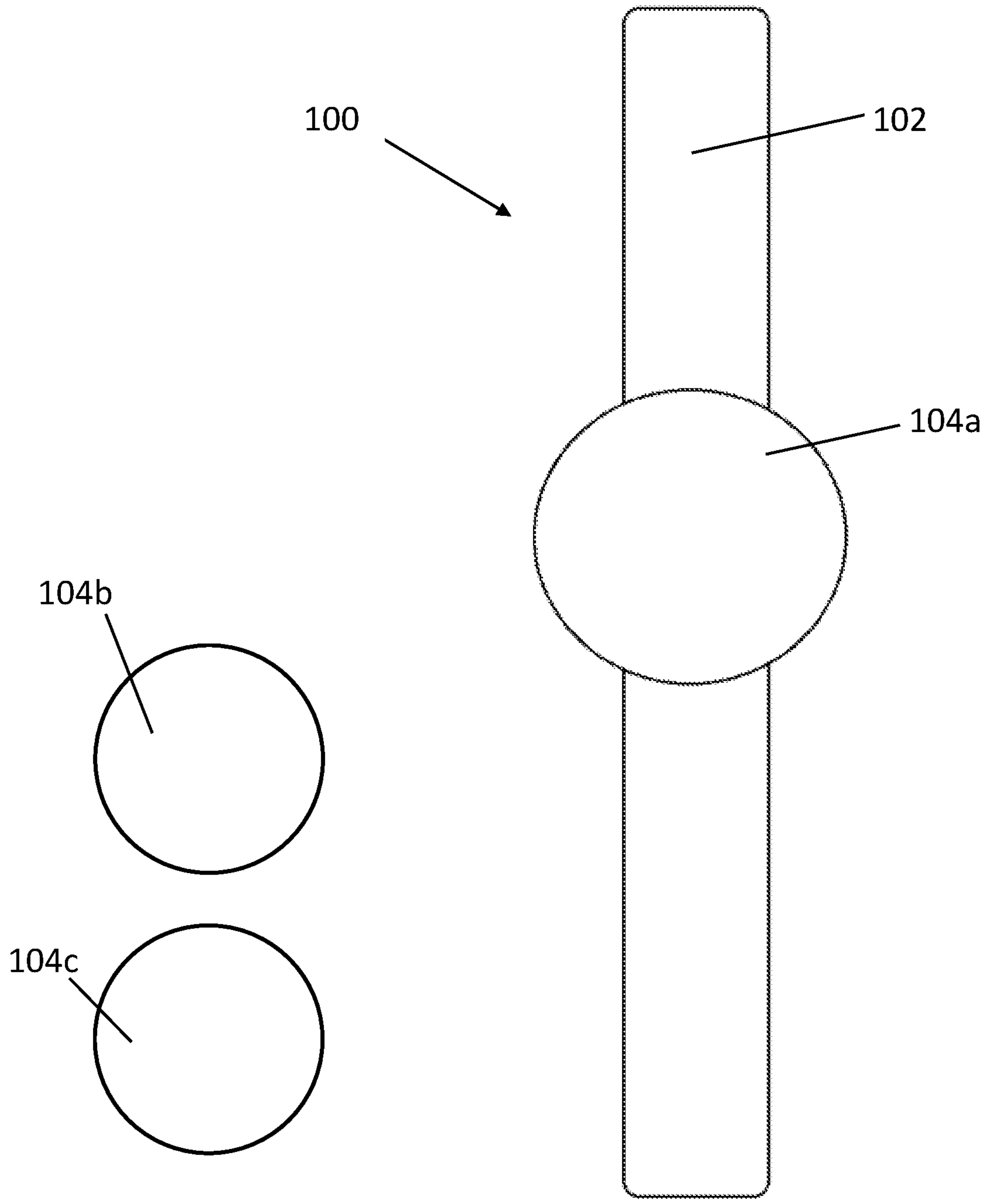
FIG. 1 is a schematic showing features of an orthosis system according to an embodiment of the present invention.

FIG. 1 is a schematic showing features of an orthosis system 100 or exoskeleton according to an embodiment of the present invention. The system 100 comprises a body mounting module 102 configured to, in use, be mounted to a part of a body of a patient, and a plurality of function or sensing/control modules 104*a*, 104*b*, 104*c*. The sensing/control modules 104 are configured to be removably and interchangeably coupled to the body mounting module 102 so that any of the sensing/control modules 104 may be selectively mounted to the body mounting module 102. FIG. 1 illustrates sensing/control module 104*a* mounted on the body mounting module 102. In other embodiments (including those described later) multiple sensing/control modules 104 are able to be mounted to the body mounting module 102 at any one time. In yet further embodiments, there may be provided a plurality of body mounting modules and one or more functions modules configured to be interchangeably coupled to the body mounting modules.

It will be understood that a function or sensing/control module 104 is a device or assembly of components that performs a sensing and/or control function. Any one of the sensing/control modules 104 may perform a sensing function, a control function or a combination of sensing and control functions.

It will be understood that embodiments of the orthosis system herein disclosed may be configured as a brace for any part of a patient's body. While the preferred embodiments relate to a knee brace and an elbow brace, the orthosis system of the present invention may alternatively be configured as, for example, a wrist, elbow, shoulder or ankle brace with suitable adaptations to the shape and size of the components of the orthosis system. The patient may be a human or animal patient.

In other embodiments, the technology described in the exemplary embodiments of the invention may be incorporated into other types of rehabilitation or patient assistance devices, for example crutches and walking sticks.

Embodiments of the invention will be described comprising rigid frame elements providing structural support to the orthosis system or brace and softer and/or less rigid pad elements providing comfort to those parts of the system in contact with the patient. In alternative embodiments the body attachment module comprises a fabric-based brace or wearable garment to be worn under clothing or strapping to remain more lightweight, for example for wearing throughout the day when less injured.

Knee Brace

Figure 2A:
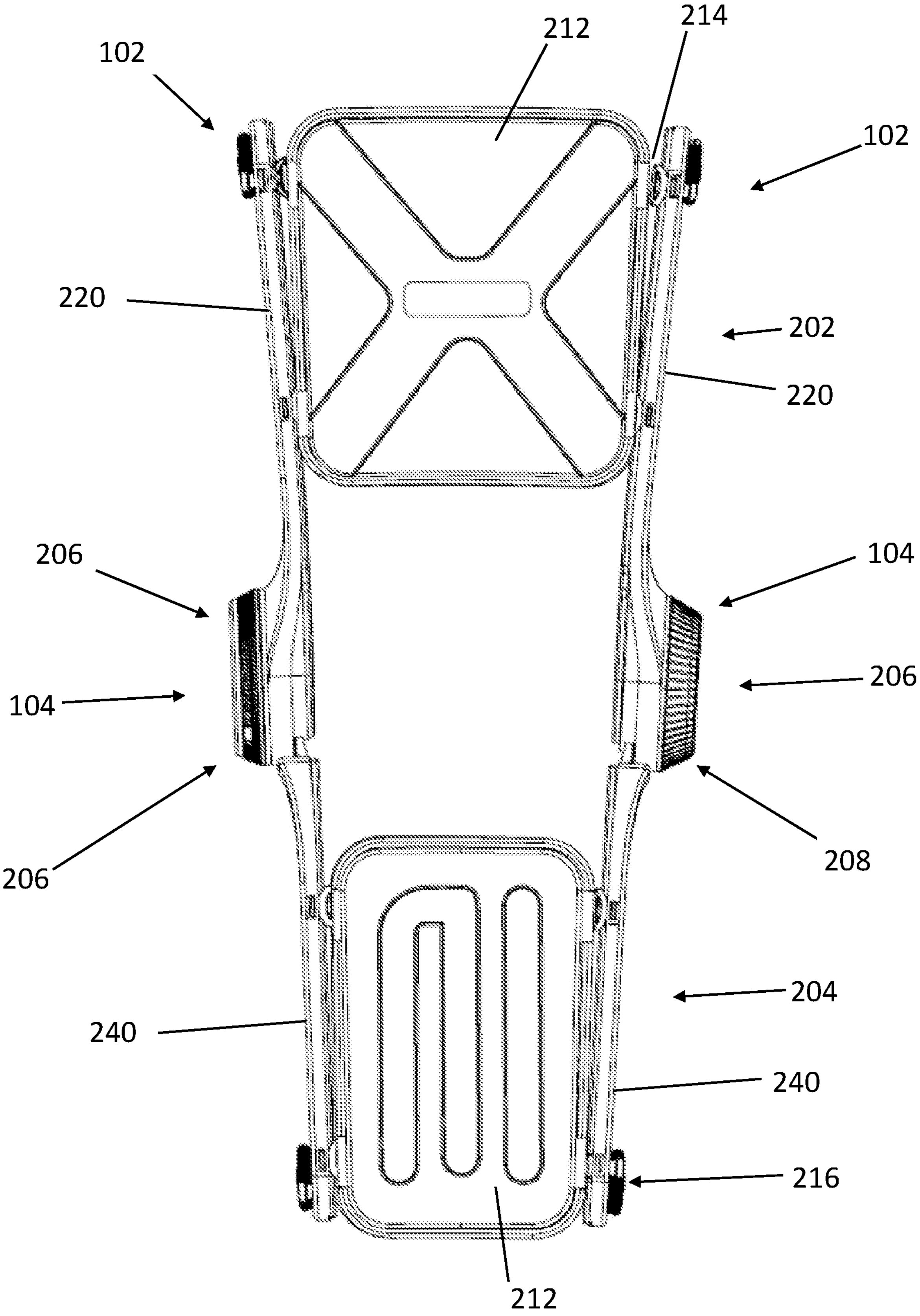
FIG. 2A is a front view of an assembled orthosis system according to an embodiment of the present invention.
Figure 2B:
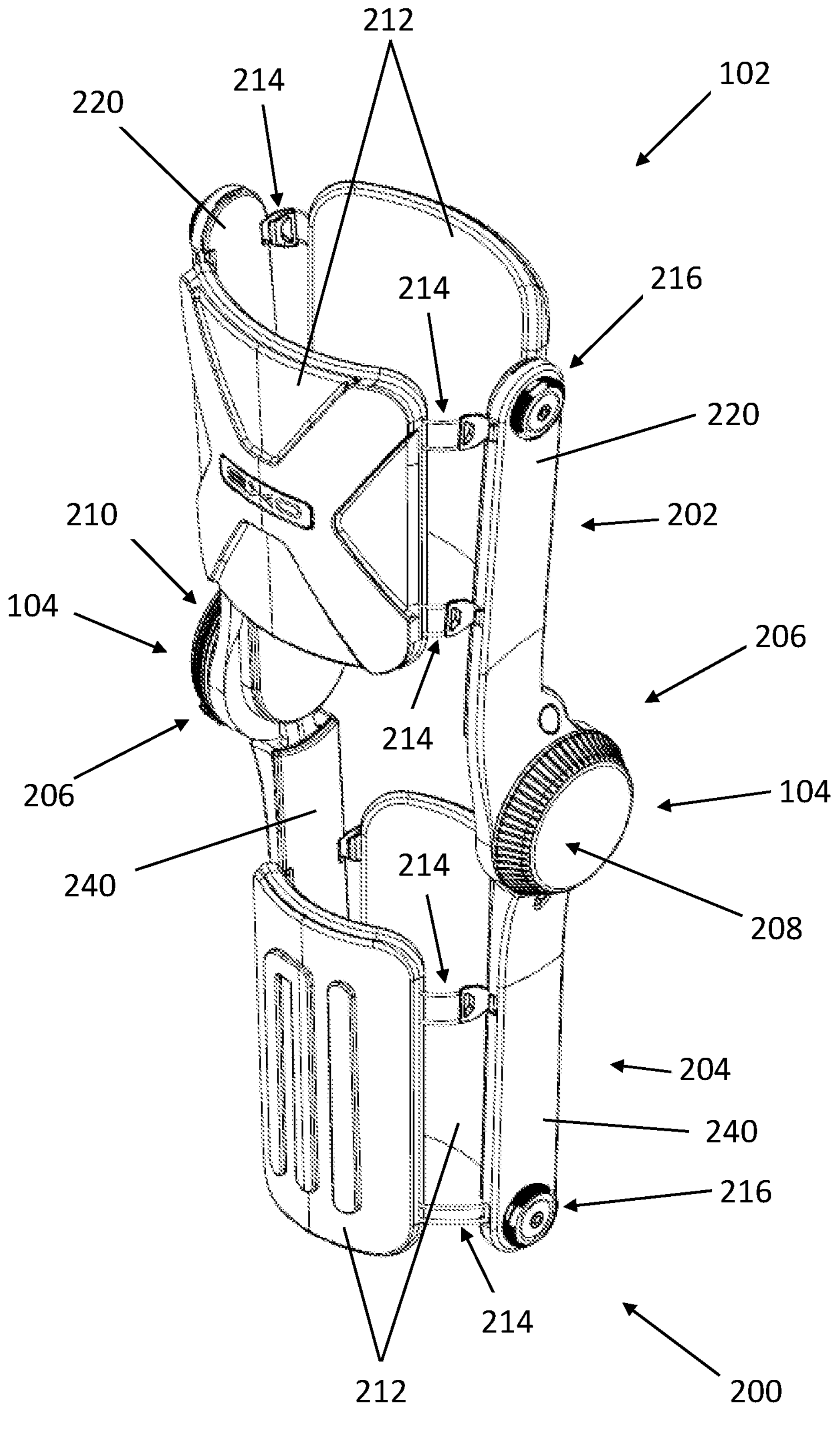
FIG. 2B is a profile view of the orthosis system of FIG. 2A.

FIGS. 2A and 2B show an assembled orthosis system 200 according to a preferred embodiment of the present invention. Orthosis system 200 is particularly suited for mounting proximate a knee (not shown) of the patient (not shown).

In this embodiment, a body mounting module 102 comprises a first brace assembly 202 and a second brace assembly 204. In use, the first brace assembly 202 is mounted upwardly of the knee of the patient and the second brace assembly 204 is mounted downwardly of the knee of the patient.

The second brace assembly 204 is pivotably coupled to the first brace assembly 202 via pivot assemblies 206. This makes the orthosis system 200 suited to use in bracing a pivoting joint of the body, such as the knee. In other embodiments of the invention the first and second brace assemblies are moveably coupled in some other manner, for example through a sliding coupling. Such embodiments may be suitable for use in bracing an extendable part of the body, for example.

In the embodiment of FIGS. 2A and 2B the first brace assembly 202 comprises a frame comprising two frame elements 220. Frame elements 220 are elongate and, in use, are positioned on either side of the portion of the patient's leg immediately above the knee. Frame elements may be formed from a structurally rigid material such as metal, alloy or a rigid plastics material, or a combination of materials. Second brace assembly 204 comprises a frame comprising two frame elements 240. Frame elements 240 are elongate and, in use, are positioned on either side of the portion of the patient's leg immediately below the knee. Frame elements 240 are typically made of the same material as frame elements 220.

Frame elements 220 each comprise a first pivot portion at their lower end (i.e. at an inferior end when the orthosis system 200 is being worn by a patient), and frame elements 240 each comprise a second pivot portion at their upper end (i.e. at a superior end when the orthosis system 200 is being worn by a patient). The first and second pivot portions form part of, and are pivotably coupled at, the pivot assemblies 206.

In this embodiment, the sensing/control modules in the form of a sensing module 208 and a control module 210 may be provided. The sensing and control modules 208, 210 are removably coupled to the pivot assemblies 206 of the body mounting module 102 on either side of the orthosis system 200 so that, when the orthosis system 200 is being worn the sensing module 208 is on one side of the patient's knee and the control module is on the other side of the knee. In other embodiments the orthosis system is configured to mount sensing/control modules in other positions in relation to the body.

In the embodiment of FIG. 1, the body mounting module 102 comprises at least one pad 212 configured to contact the body of the patient (in particular the leg of the patient) in use. The pads 212 may be made of a semi-rigid or soft material to support the orthosis system 200 on the body of the patient in a comfortable manner.

Orthosis system 200 may comprise a plurality of pads 212 configured to be removably and interchangeably coupled to the frame. This enables pads of different sizes, shapes, colours and/or textures to be selectively mounted on the frame for use, depending on the needs of a patient or their clinician. The pads may be different colours and carry different aesthetic designs as chosen by the customer to provide customisation. A specific patient may be able to design their own aesthetic design via a drawing submitted by various means, including but not limited to a web or mobile app, which can then be manufactured and sent to the patient. Interchanging pads 212 may be beneficial since the pads 212 are in contact with the patient's body during use they may be prone to becoming dirty or worn and consequently need regular washing and/or replacement.

The pads 212 are removably coupled to frame elements 220 or 240 of the body mounting module 102 via pad connectors 214. Pad connectors 214 may enable the orientation and/or position of the pads 212 to be adjusted with respect to the frame elements 220 and 240. This enables the pads to be adjusted to fit different size and shape patients comfortably. Pad connectors 214 may be configured to enable removal and re-attachment of the pads 212 to the frame.

In each attachment zone to the human limb of the body mounting module, i.e. separately for the thigh and shank in FIG. 2A, the front and back pads are individually adjusted relative to the structural support of the orthosis. This allows the patient to easily adjust the alignment of the structural support to be parallel to the limb segment. This provides more comfort, less slippage and better transfer of force/torque between the limb and the orthosis during exercise and more accurate sensor readings e.g. for joint angle. These adjustments may use a micro-adjustment system so as to allow quick and easy adjustment while the system is worn, without the need to take it off and fully readjust, and also provides accurate adjustment.

In the embodiment of FIG. 1, the pad connectors 214 each comprise a wire that, in use, engages with a ratchet mechanism 216. Ratchet mechanism 216 is configured to adjust the orientation/position of each of the pads 212 relative to the frame elements 220/240 of the body mounting module 102 when the pads 212 are coupled to the frame via the pad connectors 214. The ratchet mechanism 216 may be operated by turning a wheel. Accordingly, the pads may be adjusted in situ to suit the dimensions and contours of the relevant body part of an individual patient to provide the patient with a correct fit and appropriate support. The system of the present invention is thus versatile and easily adaptable. In other embodiments of the invention the pad connectors 214 may take other forms, for example hook-and-loop fasteners (e.g. Velcro), buckles, snap-fit connectors, ties, domes, poppers, etc.

Pivot Assembly

Figure 3A:
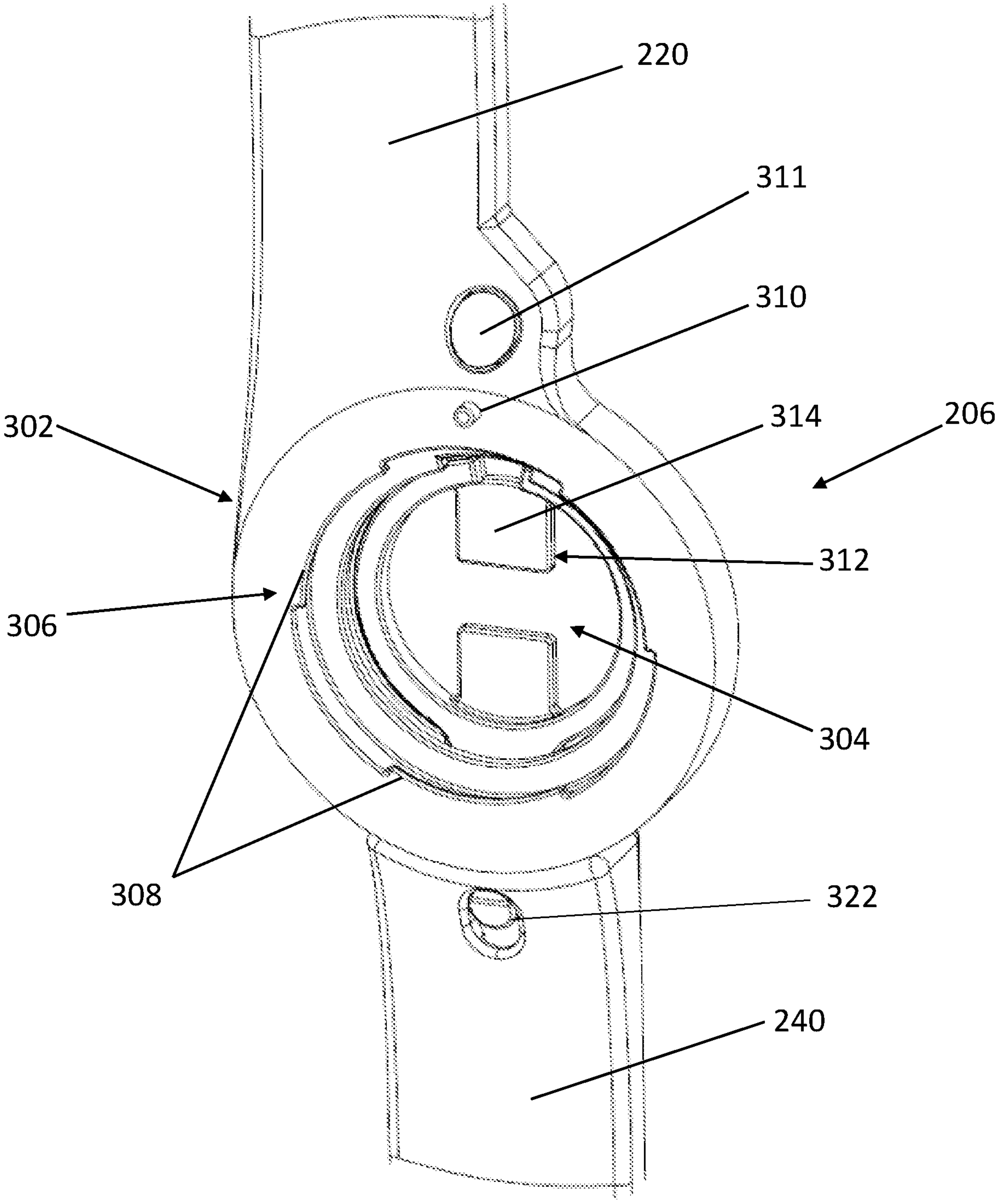
FIG. 3A is a detailed view of the pivot assembly of the embodiment of FIG. 2A.

FIG. 3A shows a detailed view of one of the pivot assemblies 206 of the embodiment of FIG. 2A. Frame element 220 of first brace assembly 202 comprises a first pivot portion 302, and the frame element 240 of second brace assembly 204 comprises a second pivot portion 304, the first and second pivot portions 302, 304 forming part of and being pivotably coupled at the pivot assembly 206.

FIG. 3A also shows the interfacing structure by which the pivot assembly 206 according to this embodiment of the orthosis system is configured to enable the sensing/control modules (not shown in FIG. 3) to removably couple thereto.

The first pivot portion 302 comprises a first brace interfacing structure 306 and the second pivot portion 304 comprises a second brace interfacing structure 312. Although not shown in FIG. 3A the sensing/control modules each comprise a module interfacing structure (described below) which is configured to, in use, interface with both the first brace interfacing structure 306 and the second brace interfacing structure 312. By sensing/control module 104 interfacing with both the first brace interfacing structure 306 and the second brace interfacing structure 312, particularly advantageous sensing and/or control functions are provided, such as will be described below.

In other embodiments the sensing/control module 104 may be coupled to the body mounting module at a location other than the joint between brace assemblies. For example, the sensing/control module 104 may be coupled to the body mounting module such that it interfaces with only the first brace interfacing structure 306 or the second brace interfacing structure 312.

First brace interfacing structure 306 comprises at least a first flange 308. In the embodiment of FIG. 3A there are a plurality of first flanges 308 arranged circumferentially around a circular opening. The first flanges 308 project radially inward from an annular surface of the first pivot portion 302 and are separated by spaces. As will be described later, first flanges 308 interface with flanges on the sensing/control modules to couple the sensing/control modules to the first brace assembly 202.

First brace interfacing structure 306 further comprises a first brace locking element 310. In this embodiment, the first brace locking element 310 comprises a spring-biased depressible button biased in an outward direction configured to mate with a hole on the sensing/control module to lock the orientation of the sensing/control module relative to the first brace assembly 202, as will be described further later in this specification. In the embodiment shown, the button of locking element 310 projects perpendicularly outward from the plane of the facing surface of the first pivot portion 302. In this embodiment, the first brace locking element 310 is operatively coupled to a release mechanism comprised by the first brace assembly 202. In use, pushing a button 311 activates the release mechanism and causes the first brace locking element 310 to be retracted.

Second brace interfacing structure 312 comprises a second brace locking element 314. In this embodiment, the second brace locking element 314 comprises a pair of approximately square protrusions spaced apart to form a 'H'-shaped recess. As will be described later the square protrusions are configured to interface with correspondingly shape recesses on the sensing/control modules to lock the orientation of the sensing/control modules to the second brace assembly 202.

The orthosis system may comprise a movement prevention mechanism configured to be selectively activated to prevent movement of the first brace assembly relative to the second brace assembly. In the embodiment of FIG. 3A, for example, the second brace assembly 204 comprises a rotation prevention mechanism configured to prevent relative rotation of the first and second brace assemblies. The rotation prevention mechanism (not shown in detail in FIG. 3A) may comprise a moveable locking member on one of the first and second brace assemblies that engages with a stop on the other of the first and second brace assemblies to prevent rotation of the brace assemblies. The rotation prevention mechanism may be engaged or disengaged by movement of switch 322.

Frame Elements

Figure 3B:
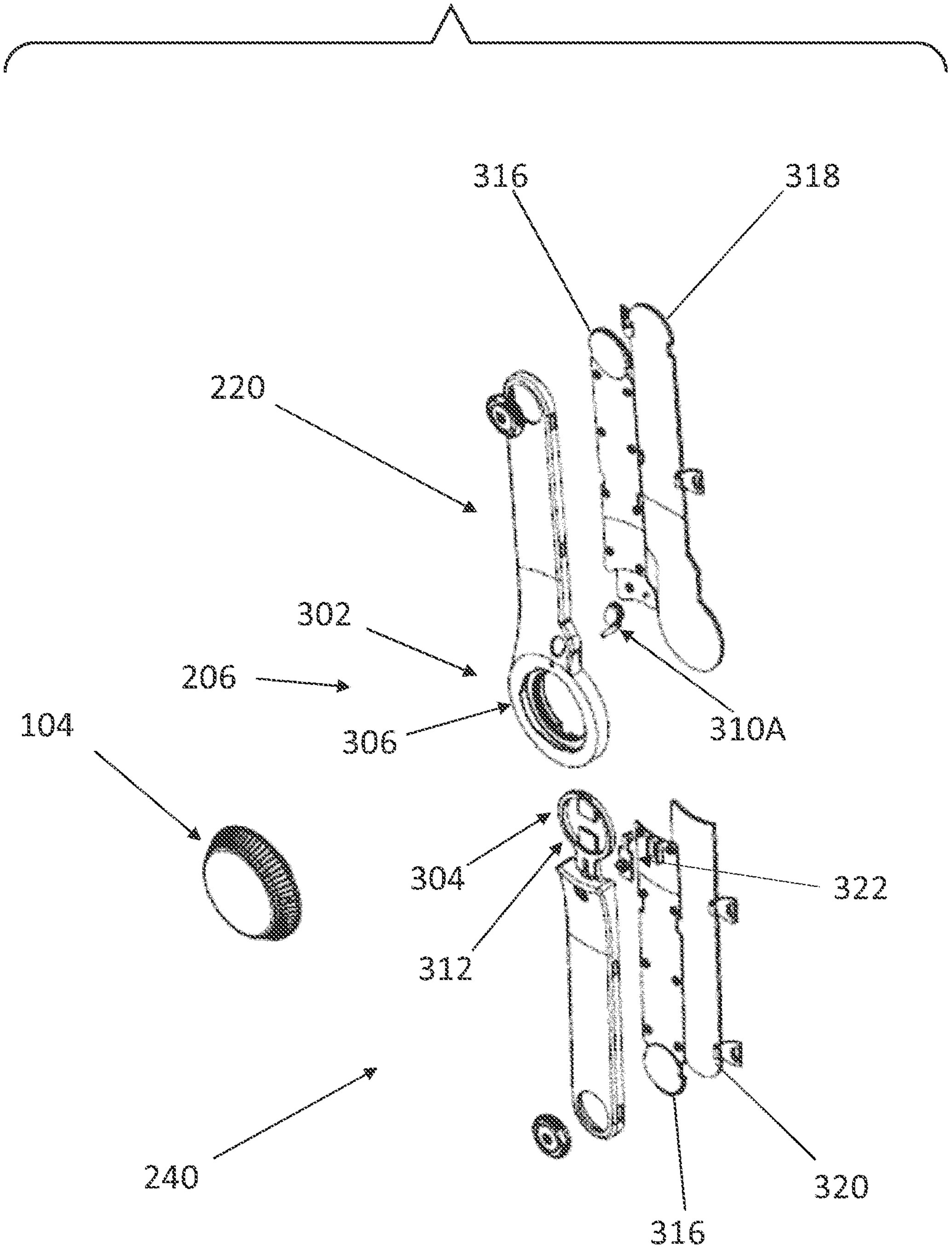
FIG. 3B is an exploded view of a part of the orthosis system 200 of the embodiment of FIG. 2A.

FIG. 3B is an exploded view of a part of orthosis system 200. FIG. 3B shows the construction of the first and second frame elements 220 and 240 and the configuration of the pivot assembly according to this embodiment of the orthosis system in more detail. A sensor/control module 104 is also shown in FIG. 3B.

It will be seen that the first and second frame elements 220 have a composite construction and comprise reinforcing layers 316 and inner layers 318, 320. In this embodiment, the inner layer 318 of the first frame element 220 comprises EVA foam pads. This may be conducive to the comfort of the patient by providing a relatively soft and/or flexible surface that contacts the patient's body in use.

When the orthosis system is assembled, the second pivot portion 304 on the second frame element 240 is disposed between the first pivot portion 302 and the inner layer 318 of the first frame element 220, such that the first and second frame elements are pivotally moveable relative to one another. In another embodiment the configuration of the pivot assembly may be reversed.

It can also be seen in FIG. 3B that the depressible button of the first brace locking element 310 is of unitary construction with the release button 311.

Sensing/Control Module

Figure 4A:
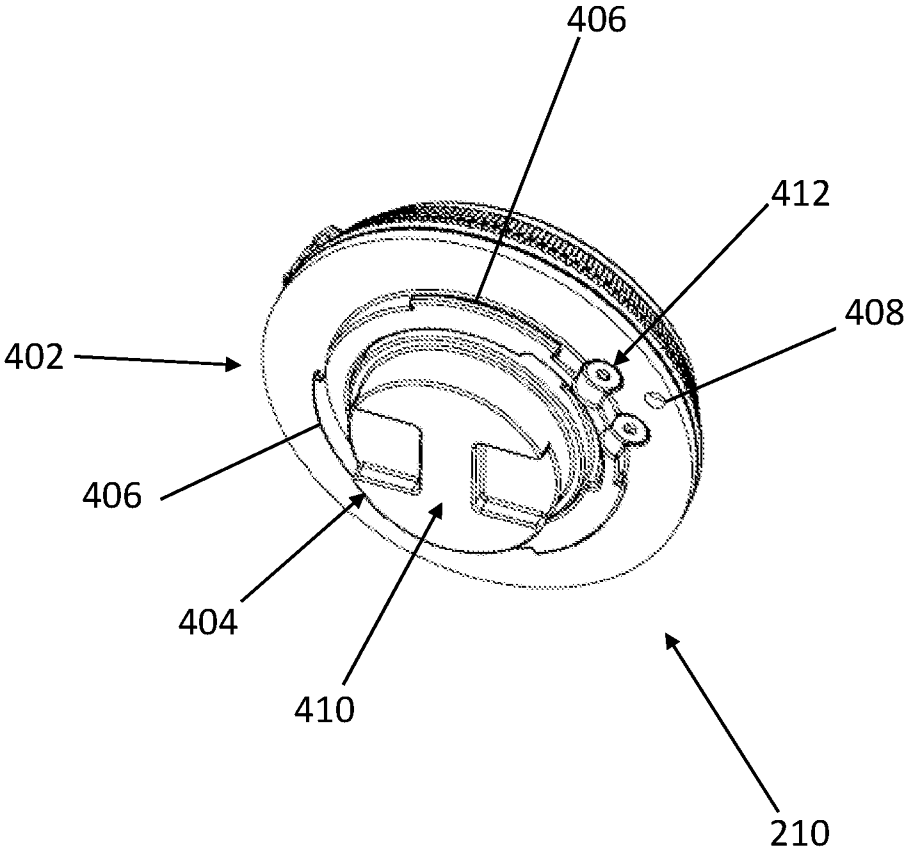
FIG. 4A is a perspective view of a control module according to an embodiment of the present invention.
Figure 4B:
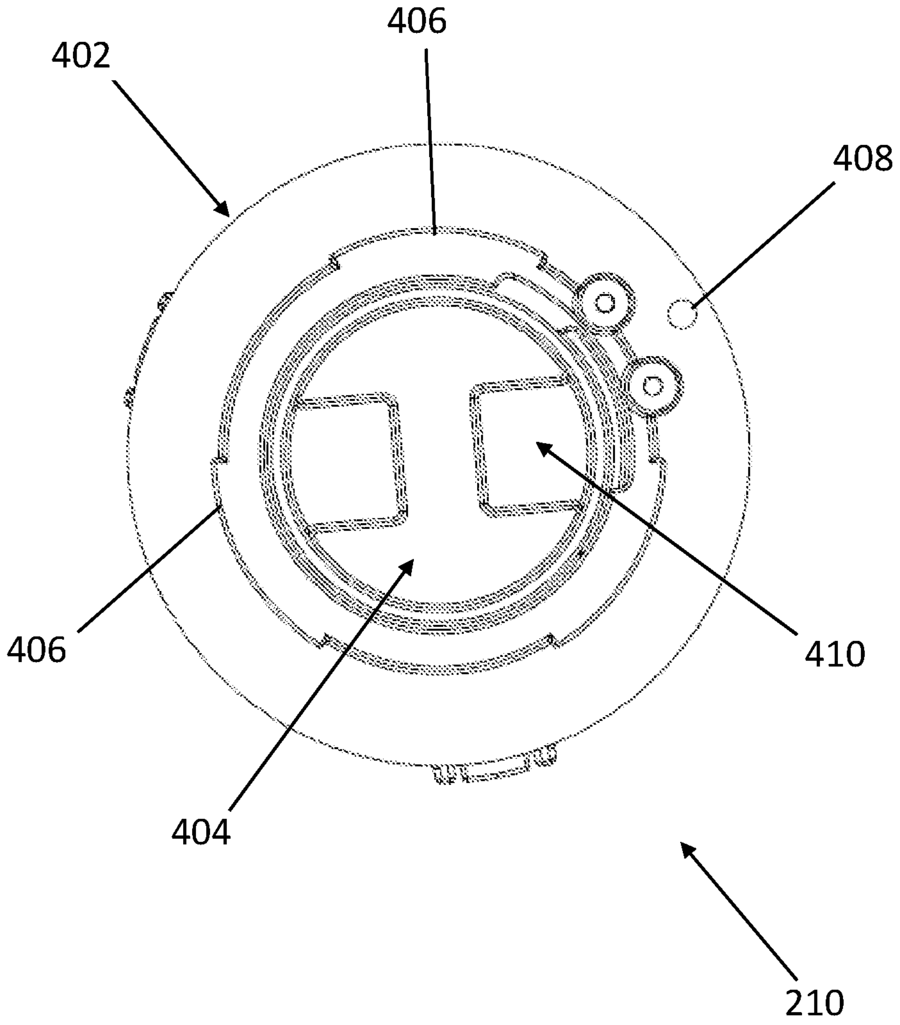
FIG. 4B is a bottom view of the control module of FIG. 4A.

FIGS. 4A and 4B show an exemplary control module 210 according to a preferred embodiment of the present invention. The control module 210 comprises a first module portion 402 and a second module portion 404, the first 402 and second 404 module portions being configured to rotate relative to each other in use.

The control module 210 also comprises a module interfacing structure comprising at least one second flange 406 on the first module portion 402. The second flange 406 projects radially outwardly from a neck portion extending out from the inner surface of first module portion 402 (i.e. the side facing the viewer in FIG. 4A) such that there is a gap between the second flange 406 and the inner surface of the main body of first module portion 402. Multiple second flanges 406 may be provided, each separated by a spacing. The second flanges 406 are configured to be complementary to the first flanges 308 on the first brace interfacing structure of the first brace assembly shown in FIG. 3A so that the second flanges 406 fit through the spaces between first flanges 308.

The module interfacing structure also comprises a locking aperture 408 on the inner side of the first module portion 402. The locking aperture 408 is configured to be able to receive the button comprising the locking element 310 on the first brace interfacing structure. Accordingly, the locking aperture 408 and the depressible button of locking element 310 together form a first locking mechanism which, when the orthosis system is assembled, locks the orientation of the first module portion 402 of the control module 210 to the first pivot portion, and therefore to frame element 220 and the first brace assembly 202.

The module interfacing structure further comprises a locking formation 410 on the second module portion 404. The locking formation 404 comprises one or more raised sections complementary in shape to the second brace locking element 314 on the second brace interfacing structure 312 of the second brace assembly 204. In this embodiment, the locking formation 404 comprises a pair of approximately square depressions and an 'H'-shaped protrusion complementary to the pair of approximately square protrusions an 'H'-shaped recess comprising the second brace locking element. Accordingly, the locking formation 404 and protrusions together form a second locking mechanism which, when the orthosis system is assembled, locks the orientation of the second module portion 404 of the control module 210 to the second pivot portion, and therefore to frame element 240 and the second brace assembly 204.

Connection of Sensing/Control Module to Pivot Assembly

In use, the control module 210 is coupled with the pivot assembly 206 by moving the control module 210 towards the pivot assembly generally in the direction perpendicular to the plane of the control module 210 and the facing surface of the pivot assembly 206. The control module 201 is oriented such that the first flanges 308 on the first brace interfacing structure 306 align with the gaps between the second flanges 406 on the first module portion 402. Complementary markings (not shown) on the control module 210 and first pivot portion may be provided to assist the user to correctly orient the control module 210 in this regard.

The second brace locking element 314 and locking formation 410 on the second module portion 404, which in this embodiment comprise complementary pairs of approximately square depressions and protrusions, also engage, thereby rotatably coupling the second module portion 404 to the second brace assembly 204.

The first module portion 402 is then rotated, causing the second flanges 406 to interlock with the first flanges 308, securing control module 210 to the body mounting module 102. The first module portion 402 continues to be rotated until the depressible button 310 on the first brace interfacing structure aligns with the locking aperture 408 on the first module portion 402 and, due to the spring-bias the button 310 mates with the locking aperture 408. This rotatably couples the first module portion 402 to the first brace assembly 202.

As noted above, the first 402 and second 404 module portions are rotatable relative to one another. Thus once coupled to the first and second brace assemblies (respectively), the first 402 and second 404 module portions are able to rotate with the respective brace assemblies or, in some embodiments, to cause the respective brace assemblies to rotate relative to each other.

In order to disengage the control module 210 from the body mounting module 102, the release button 311 on the first brace assembly is pushed down by the patient. This causes the locking element 310 of the first brace interfacing structure to retract and disengage from the locking aperture 408. The first module portion 402 may then be rotated to disengage the second flanges 406 from the first flanges 308, allowing the control module 210 to be removed.

Figure 5A:
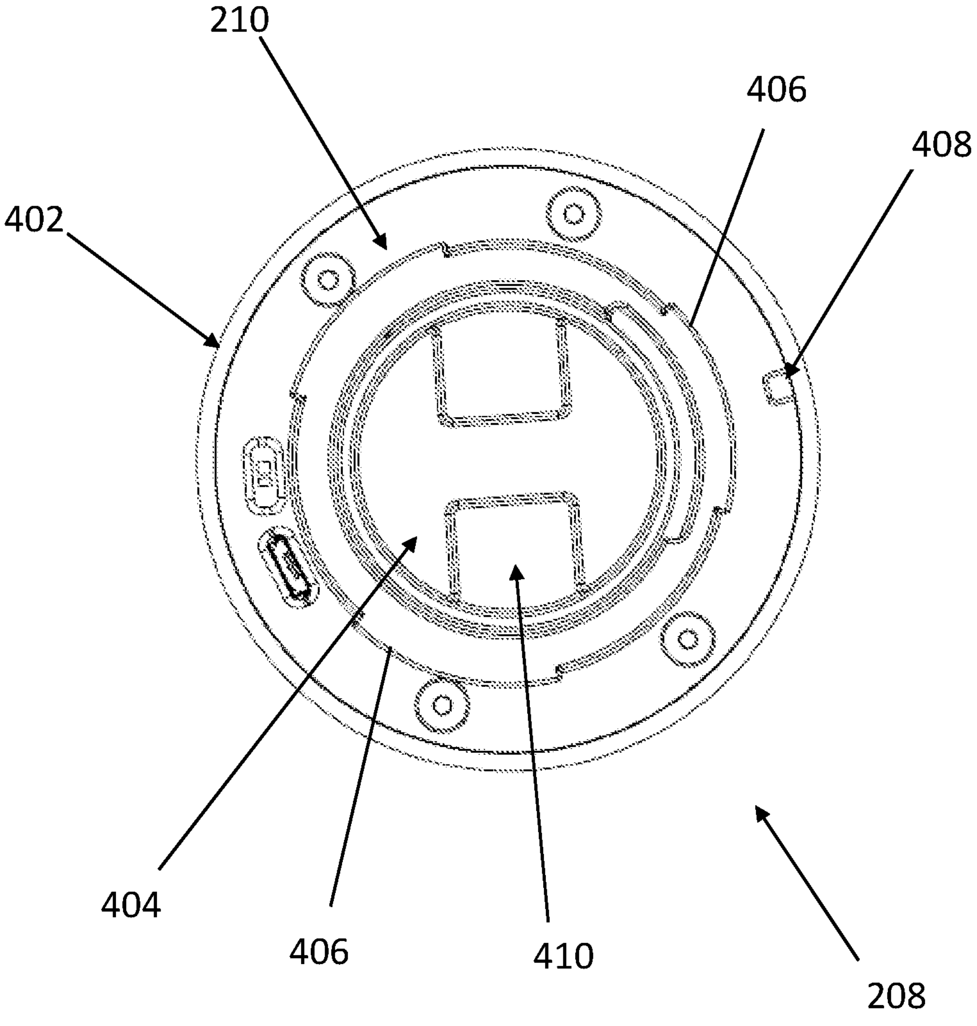
FIG. 5A is a bottom view of a sensing module according to an embodiment of the present invention.

FIG. 5A shows a sensing module 208 according to a preferred embodiment of the present invention. The sensing module 208 is configured to couple to the pivot assembly of FIG. 3A in substantially the manner described in relation to the control module of FIGS. 4A and 4B. Accordingly, like features are assigned a like numeral.

This enables multiple sensing or function modules 208 to be interchangeably coupled to a particular body mounting module 102, multiple body mounting modules 102 to be interchangeable coupled to a particular function module 2088, or multiple body mounting modules 102 and multiple function modules 208 to be interchangeably coupled with each other.

It will be understood that the above-discussed embodiment is given by way of example only, and that other configurations may also be employed to couple the control/sensing modules to the body mounting module. For example, screws or similar fastening means may be employed, straps, hook-and-loop fasteners, and/or magnets. In one alternative embodiment a snap-fit arrangement is provided to couple the sensing/control module to the pivot assembly. In another embodiment a spring-loaded push-in mechanism is used, so that the sensing/control module is pushed against the pivot assembly once to couple the two assemblies together and then pushed together again to disengage them.

Rotation Limitation Module

Figure 4C:
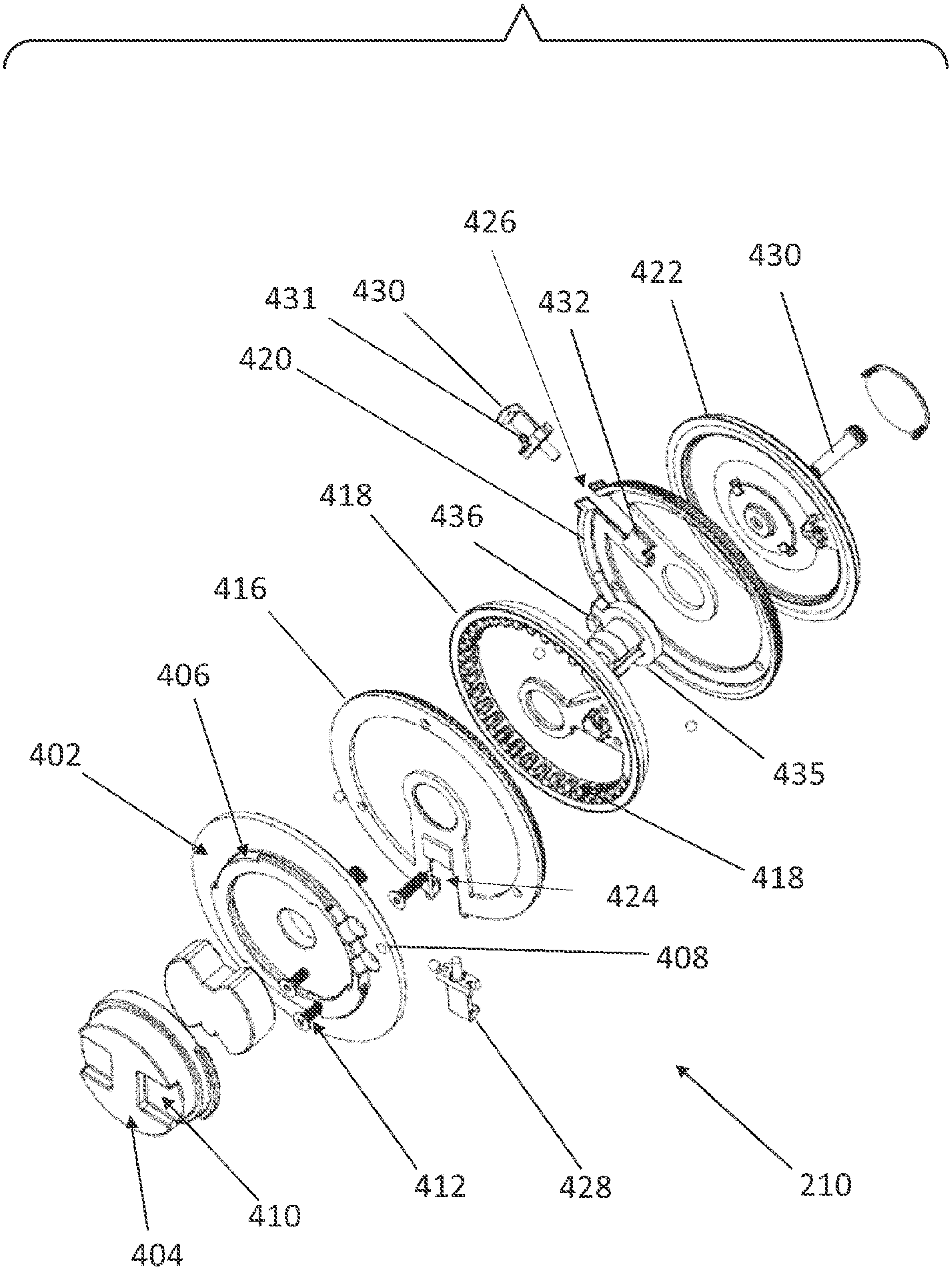
FIG. 4C is an exploded view of the control module of FIG. 4A.

One exemplary sensing/control module is a rotation limitation module. FIG. 4C shows an exploded view of the such a rotation limitation control module 210, the underside of which is similar to the control module 210 shown in FIG. 4A. In addition to the components described above, the control module 210 further comprises a top plate 420, a bottom plate 416, and an exterior housing 422, the various components being held together by screws 412 when assembled. Other fastening means may also be used, for example other fasteners, snap fit structures or the like.

The control module 210 further comprises a rotation limitation mechanism, which will now be described. A middle plate 418 includes a plurality of teeth 418A circumferentially arranged about a peripheral surface. In the embodiment shown, the teeth 418A are arranged around a radially inwardly facing surface of the middle plate 418. A pair of levers 428, 430 fit into radial grooves or slots 424, 426 in the bottom 416 and top 420 plate, respectively. A portion of each lever 428, 430 extends to the exterior of the control module 210 such that they are adjustable by a user. That is, the lever may be pushed radially inward by a user along the respective groove 424, 426. The lever is spring-biased in the radially outward direction by a spring (not shown) or other resilient member. Each lever comprises one or more teeth 431 arranged to engage with teeth 418A on middle plate 418. In the embodiment shown, teeth 431 are provided on a surface of levers 428, 430 facing radially outwards.

Figure 4D:
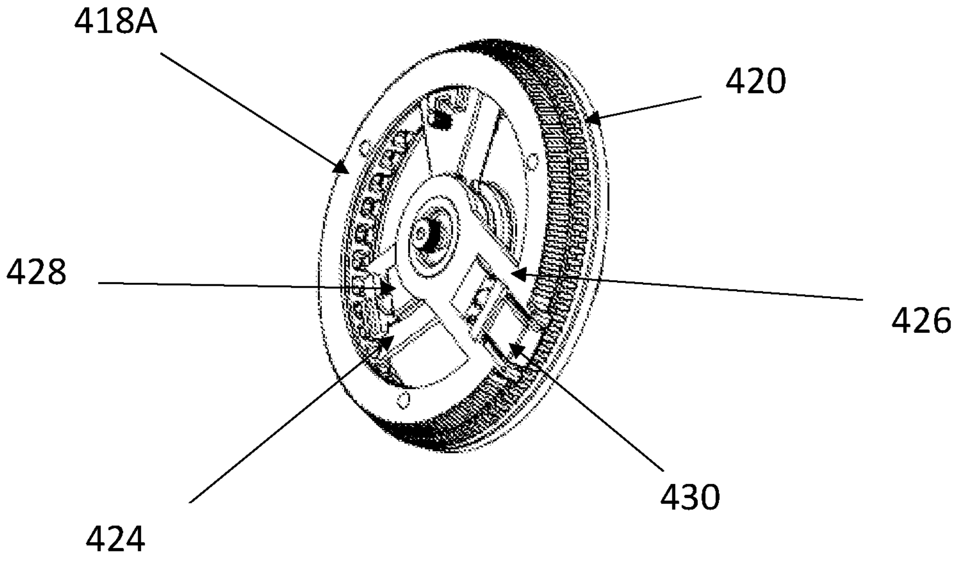
FIG. 4D is a perspective view of the partially-assembled control module of FIG. 4A, with the outer housing omitted to permit a view of the internal components of the control module.

The levers 428, 430 may be pushed inward to disengage teeth 431 from teeth 418 to enable rotation of the top and bottom plates 416, 420 around the central axle 430 of the control module 210. When released the levers are urged radially outward by their respective bias mechanisms and interlock between pairs of teeth 418A. FIG. 4D shows the levers 428, 430 locked into the teeth 418A in this manner. This prevents further rotation of top and bottom plates 416, 420.

Once the levers are locked, the circumferential position of the levers sets rotation limits that prevent rotation of the first 402 and second module 404 portions, and hence the first and second brace assemblies, relative to one another beyond the rotation limits. The relative range of rotation of the first 402 and second 404 module portion is limited to the angle between the levers 428, 430. In use, this limits the degree by which the patient may bend their leg at the knee. Top plate 420 has a stop 432 in the form of a projection on its inner surface in line with groove 426. Bottom plate 416 has a similar stop on its outer surface, although this cannot be seen in FIG. 4C. A boss 435 pivots around axle 430 and is in a fixed orientation with either the first module portion 402 or the second module portion 404. Boss 435 comprises a radially extending projection 436 having an abutment portion that, in use, abuts against stop 432 and the stop on bottom plate 416 to limit the relative rotation of the first and second module portions and the angles set by the levers 428, 430.

The exterior housing 422 may comprise a reference panel (not shown) indicating the angular displacement of the levers 428, 430 relative to one another. This assists the patient or clinician in setting the desired range of movement of the first and second brace assemblies of the orthosis system.

In the above-described embodiment the rotation limitation mechanism is manually adjusted. It will also be understood that, in other embodiments, the rotation limitation mechanism may be configured to be remotely or automatically adjusted, for example by means of an actuator provided in control module 210 and being operable to alter the angular positions of the stops 432.

Sensing Module

Figure 5B:
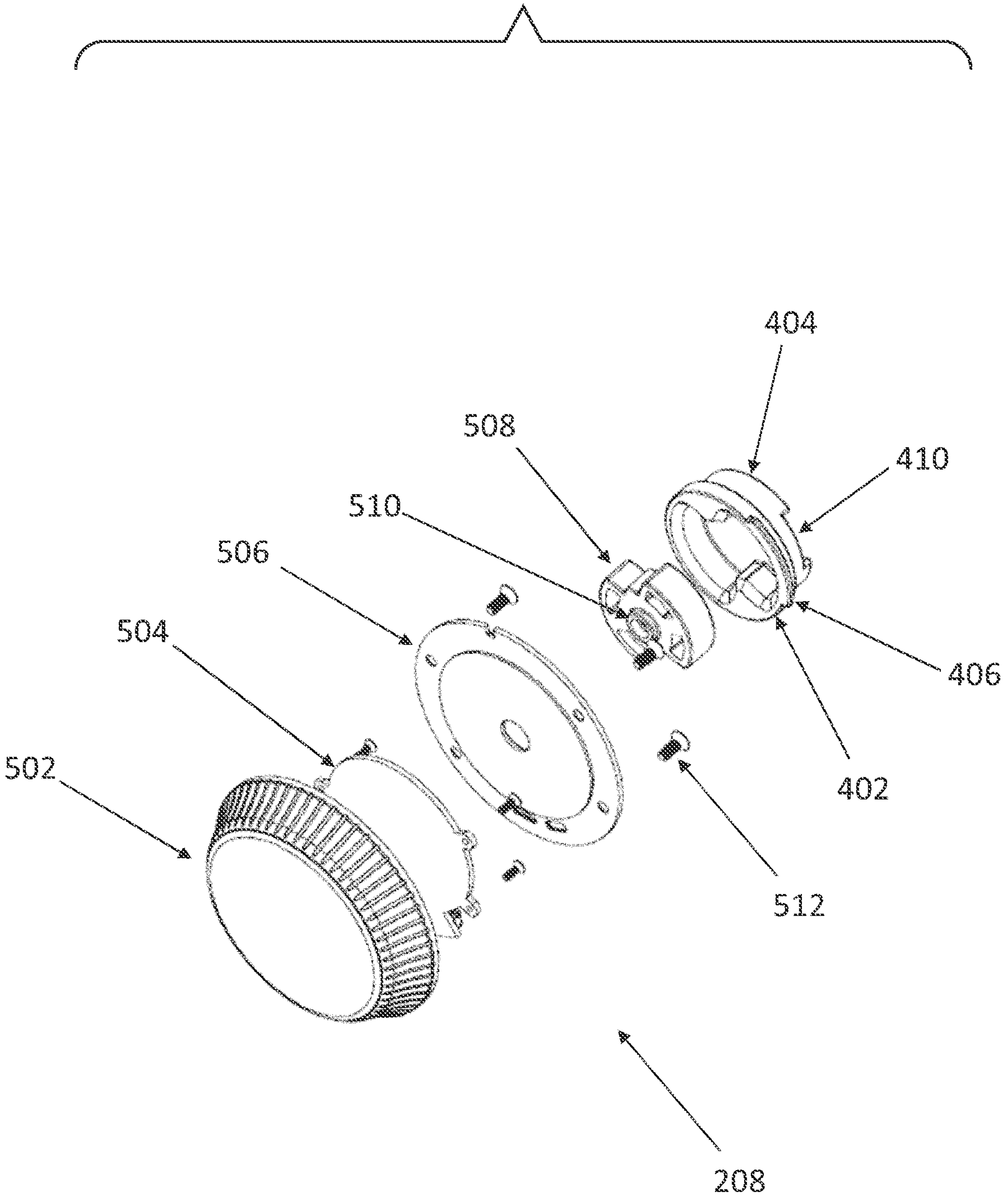
FIG. 5B is an exploded view of the sensing module of FIG. 5A.

Turning now to FIG. 5B, this shows an exploded view of the sensing module 208 of the embodiment of FIG. 5A. In addition to the components described above, the sensing module 208 comprises an exterior housing 502 and a mounting plate 506, the various components being held together by screws 512 or other fastening mechanism.

The sensing module (208) further comprises sensor components configured to detect, record, process and/or transmit data relating to the movement and/or rotation of the orthosis system or components thereof. These components may be provided on circuit board 504.

The sensor components may additionally or alternatively detect, record, process and/or transmit data pertaining to the patient's physical activity and/or physiology. This may include parameters such as joint kinematics (such as joint angle, joint velocity, joint torque, and/or joint acceleration), limb accelerations, limb rotations, limb and/or joint loads, muscle force, muscle strength, muscle velocity, electrical activity, temperature, pH, perspiration, heart rate, blood pressure and/or other bio-signals.

The sensing module 208 may comprise further components to enable the detection and recording of such data. For example, the sensing module 208 may comprise an accelerometer, gyroscope and/or magnetometers. The sensing module 208 may additionally or alternatively comprise physiological sensors, for example a thermometer, electromyography (EMG) sensor, heart rate sensor, blood pressure sensor, blood oxygen level sensor, etc.

Sensing module 208 may comprise a transmitter for transmitting data and/or signals obtained by or through the sensor components to a remote location, for example by RF, Bluetooth, Wi-Fi or any other remote communication protocol. Sensing module 208 may also comprise one or more processors configured to process the data/signals.

The sensor components may further comprise a receiver configured to receive data/signals remotely from an external source, such as external control signals.

In another embodiment, data may be stored or received by the sensing module 208 through a physical data storage device such as a memory card, USB stick or the like.

Resistance to Motion Module

In one embodiment, the sensing module 208 may comprises a resistance mechanism. A resistance mechanism is described in relation to the embodiment of FIG. 5B but it will be understood that such a mechanism may be provided in a separate module to the sensing components described in relation to FIG. 5B above.

In this embodiment, the resistance mechanism comprises a resistance member 508 form from an elastomeric material. An aperture 510 in the resistance member 508 is configured to, in use, receive a magnet (not shown). When assembled, magnetic coupling between the resistance member 508 and magnet provides a level of resistance to rotation of the second module portion 404 relative to the first module portion 402. This may be conducive to the patient exercising their knee for rehabilitative purposes. The properties of the elastomeric material of the resistance member 508 may be selected to provide a desired level of resistance to rotation.

The magnetic coupling between the resistance member 508 and magnet may also assist in securely coupling the sensing module 208 to the body mounting module.

The sensing module 208 may be configured to detect the relative movement of the resistance member 508 and magnet, thereby providing data pertaining to the patient's movement.

It will be understood that the resistance mechanism may be configured in a variety of other ways and need not necessarily comprise magnetic coupling. The resistance mechanism may be configured using electrical, mechanical, and/or inductive means. For example, the resistance mechanism may be achieved by the use of one or more compliant members such as flexible pads which provide a level of resistance on being twisted when the first and second module portions are displaced relative to each other. The resistance mechanism may also comprise an energy-dissipating mechanism such as a torsional spring or friction brake. Some configurations may enable the level of resistance to be altered in use, either manually or automatically. The skilled person will envisage various suitable configurations for the resistance mechanism.

Other Exemplary Modules

The orthosis system 100 may also comprise one or more use sensors for detecting whether the orthosis system is being used, for example if the patient is wearing the system 100. The use sensors may be provided to the body mounting module 102 and/or the sensing/control modules 104. In one embodiment, the body mounting module 102 comprises a proximity sensor to detect whether an object (e.g. that patient's body) is in close proximity to the orthosis system. In another embodiment a contact sensor may be provided on a part of the orthosis system in contact with the patient in use, for example one of the pads. The proximity and contact sensor may be configured to transmit proximity/contact data to a remote location for processing. Alternatively they may be connected to a processor comprised as part of the orthosis system.

The system 100 may also comprise a torque sensing module 104 comprising one or more sensors for monitoring joint interaction torque between the patient and the body mounting module 102. For example, such a sensor(s) may monitor relative displacement between two or more components of the system 100, for example the first and second module portions. Since the first and second module portions are coupled to the first and second brace assemblies respectively, this enables the torque sensor to sense torque between the first and second brace assemblies. The sensor(s) may be comprised in, or may be separate from, the sensing module. Torque sensing may be performed when the first and second brace assemblies are locked, or there is some resistance between them. So a torque sensing module may also incorporate a locking mechanism to substantially prevent movement (e.g. rotation) between the first and second brace assemblies, such as been described.

In other modules the form of coupling between the sensing/control module and the body mounting module may differ from the physical/mechanical coupling described in the above examples. In certain embodiments of the invention the coupling between the human attachment and functional modules may involve, but not be limited, to mechanical transfer of force/torque, displacement, electrical signals and magnetic (e.g. a Hall Effect sensor) signals, inductive power transfer, RFID and near-field communication tags.

Other types of module providing other functionality to the orthosis system may be provided in alternative embodiments. Even if such other types of module are not explicitly described as such herein, it should be understood from a description of a function that may be performed by a module that a module configured to perform that function may be provided.

Elbow Brace

Figure 6A:
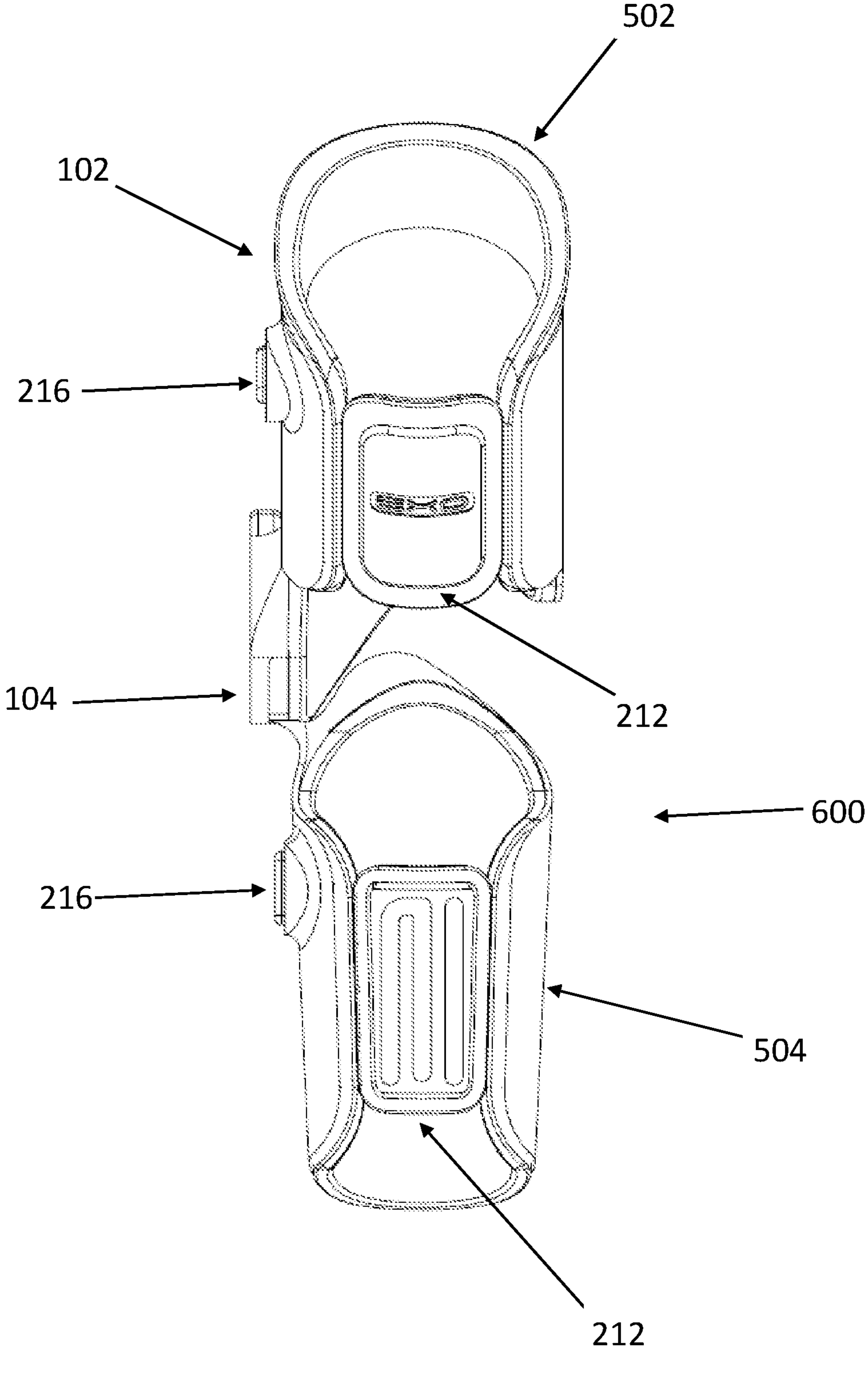
FIG. 6A is a front view of an assembled orthosis system according to another embodiment of the present invention.
Figure 6B:
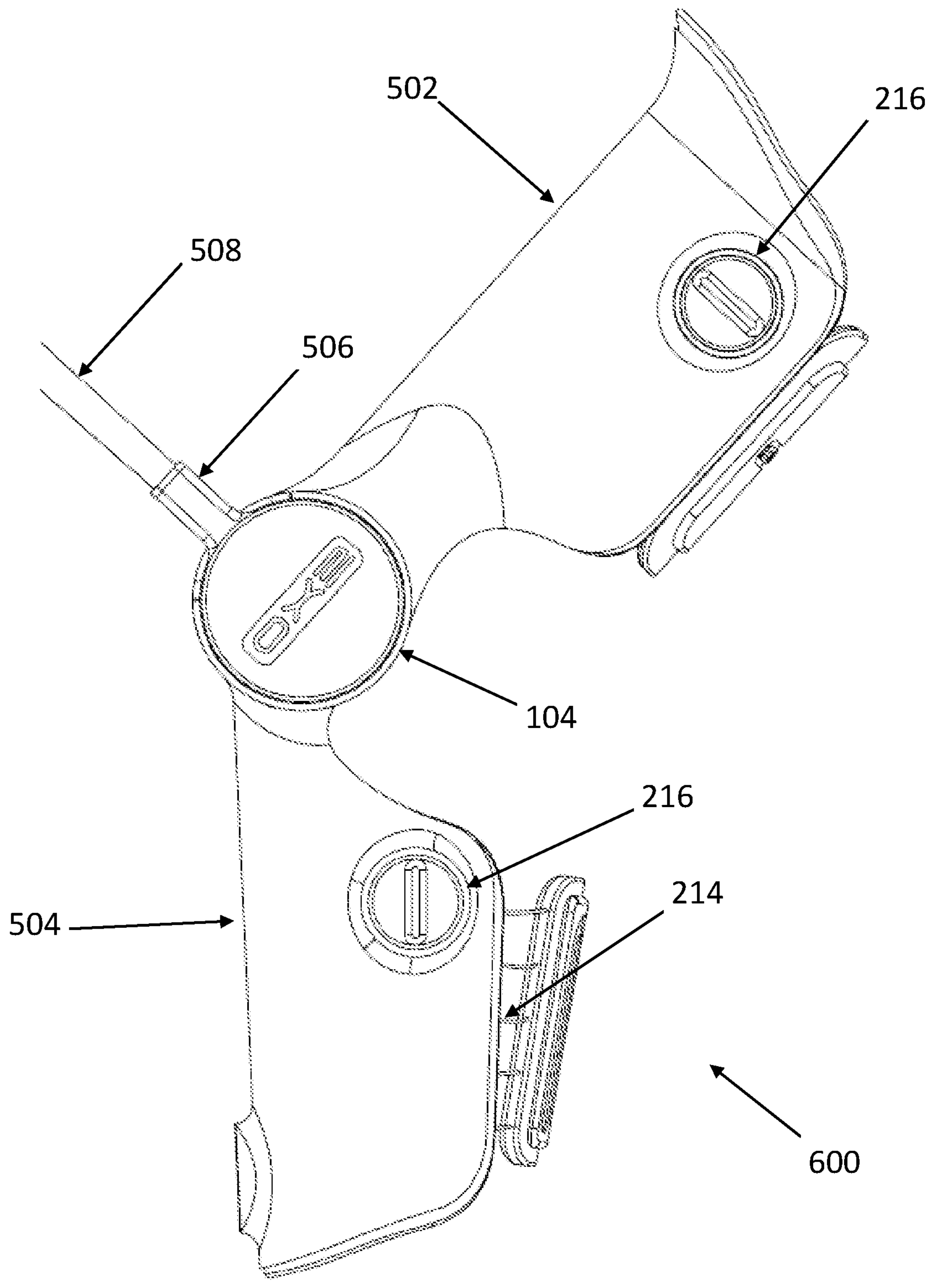
FIG. 6B is a side view of the orthosis system of FIG. 6A.

FIGS. 6A and 6B show an alternative preferred embodiment of an orthosis system 600 of the present invention, this embodiment being particularly suited for use as an elbow brace. It will be noted that the body mounting module 102 in this embodiment comprises a first brace assembly 502 configured to wrap around a portion of the patient's arm. Similarly, the second brace assembly 504 is configured to wrap around a portion of the patient's arm.

In FIG. 6B it can be seen that the sensing/control module 104 is configured with connecting means 506 to enable the sensing/control module 104 to be connected to an actuator (not shown in FIG. 6B) via a cable 508. In this embodiment, the cable 508 is a Bowden cable although other cables may be used in other embodiments. It should be noted that the embodiment of the orthosis system described in relation to FIGS. 2A and 2B may likewise comprise means for connecting the sensing/control module to an actuator.

Figure 7:
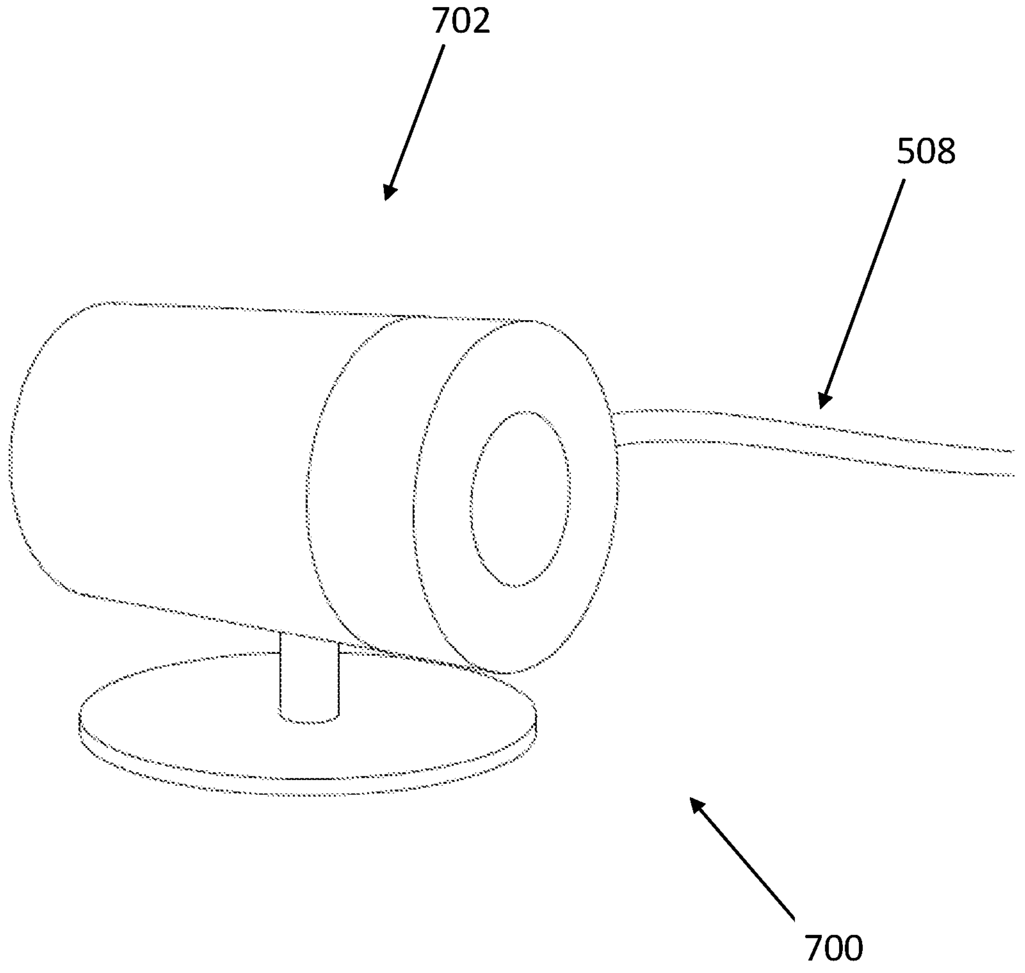
FIG. 7 is a schematic showing an actuator according to an embodiment of the present invention.

FIG. 7 is a schematic showing an actuator 700 according to a preferred embodiment of the present invention, to which the sensing/control module (not shown in FIG. 7) may be connected via the cable 508. The actuator 700 comprises a motor unit 702 configured to control movement of the orthosis system. In particular, the actuator 700 may be configured to control movement of the second module portion of the sensing/control module relative to the first module portion, thereby controlling movement of the first and second brace assemblies. The actuator 700 may for example, apply forces that assist or resist the patient's movement, as is therapeutically indicated in a given case.

It is also envisaged that in some embodiments, the actuator 700 may be configured to control the orthosis system in other ways, such as by effecting vibrotactile or neuromuscular electrical stimulation, and/or by delivering audio, haptic, and/or other signals to the patient, such as to provide real-time feedback to the patient during exercise. Such effects may be provided via an actuator provided as part of the sensing/control module in other embodiments of the invention, i.e. built-into the sensing/control module and not connected thereto by a cable or other distance-connector.

In some embodiments, the actuator 700 may also be configured to control the rotation limitation mechanism of the control module. The actuator 700 may also be configured to control the resistance mechanism of the control module, in embodiments wherein the level of resistance provided by the resistance mechanism is configured to be altered in use.

The actuator 700 may be in communication with a controller of the orthosis system configured to receive control signals, such as from a remote location.

Modular Orthosis System With Alternative Interfacing Structure

Figure 8A:
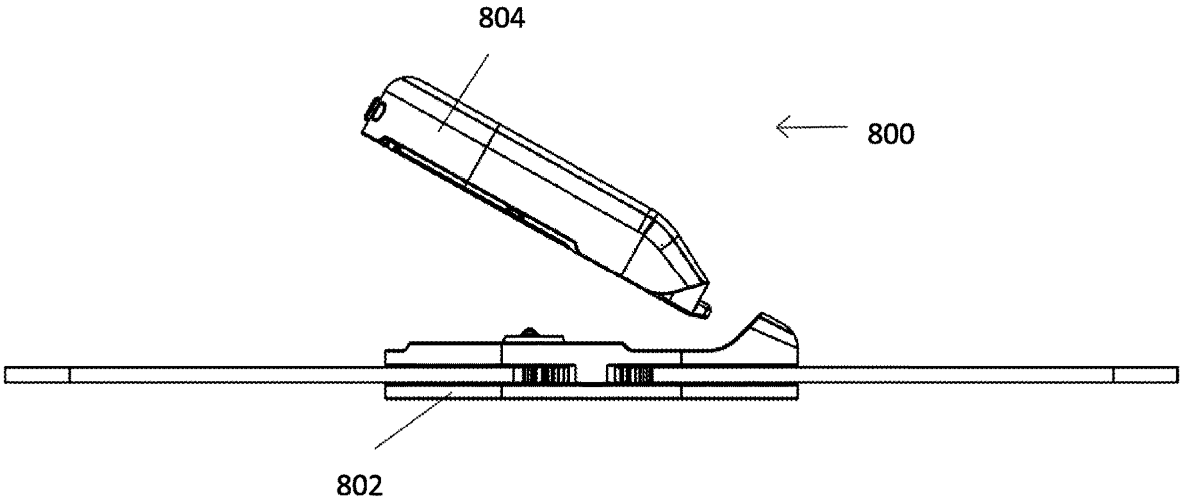
FIG. 8A is a side view of separated modules of an orthosis system according to another embodiment of the present invention.
Figure 8B:
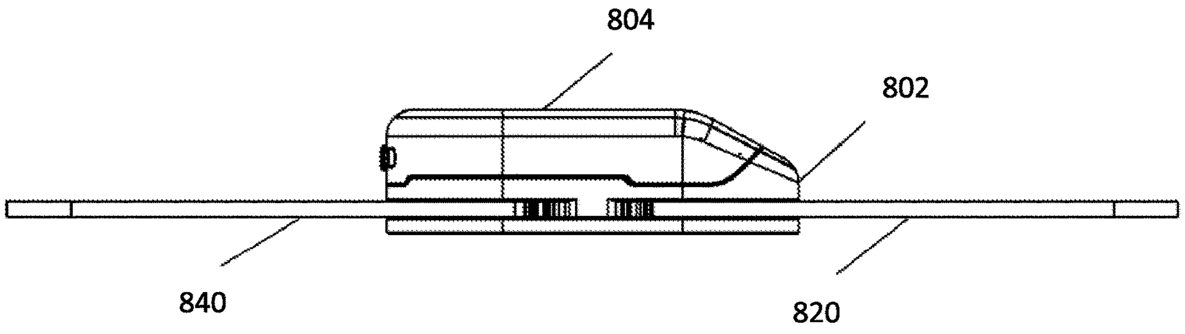
FIG. 8B is a side view of the orthosis system of FIG. 8A when the modules are coupled.

FIGS. 8A, 8B, 9, 10A, 10B and 11 show an orthosis system 800 or exoskeleton according to another embodiment of the present invention. The system 800 comprises a one or more body mounting module 802 configured to, in use, be mounted to a part of a body of a patient, and one or more function modules or sensing/control modules 804. FIG. 8A shows the function module 804 separated from the body mounting module 802, and FIG. 8B shows them coupled.

The system is modular having either or both of a plurality of body mounting modules 802 and a plurality of function modules 804. This enables multiple function modules 804 to be interchangeably coupled to a particular body mounting module 802, multiple body mounting modules 802 to be interchangeable coupled to a particular function module 804, or multiple body mounting modules 802 and multiple function modules 804 to be interchangeably coupled with each other.

It will be understood that a function module 804 is a device or assembly of components that performs a sensing and/or control and/or charging function. The different function modules 804 within the system 800 may perform different sensing, control or charging functions. Similarly, the different body mounting modules 802 within the system may be of different sizes, shapes or configurations. However the system may also include function modules or body mounting modules having similar characteristics, for example to act as spare parts in case of failure or batteries are flat or need replacing.

As with the previously described embodiments, the system 800 may be used for rehabilitation, support, or in the case of an exoskeleton implementation assistance at multiple points of the body. For ease of explanation only, this embodiment will be described in relation to use as a knee brace.

A body mounting module 802 comprises a first brace assembly 820 and a second brace assembly 840. The second brace assembly 840 is pivotably coupled to the first brace assembly 820. This makes the orthosis system 800 suited to use in bracing a pivoting joint of the body, such as the knee. In use, the first brace assembly 820 is mounted upwardly of the knee onto a thigh of the patient and the second brace assembly 204 is mounted downwardly of the knee onto a shank of the patient.

Figure 9:
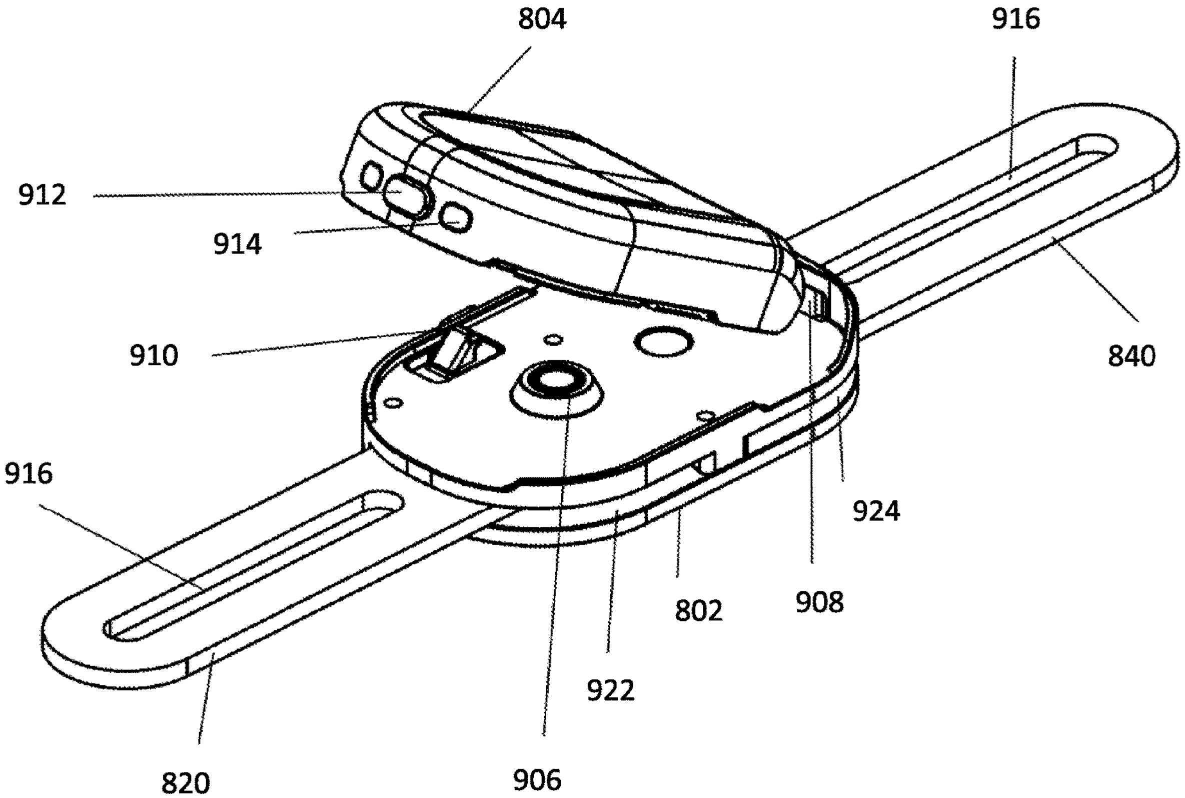
FIG. 9 is a perspective view of the orthosis system of FIG. 8A.

FIG. 9 shows a perspective view of the system 800 where the function module 804 is partly coupled to the body mounting module 802. Each function module 804 comprises securing and locating projections which are shaped to fit into complimentary locating recesses 908 in the body mounting module 802 in order to partly secure and to properly locate the function module with respect to the body mounting module. Each body mounting module 802 also comprises a sliding lock mechanism having a protruding hook 910 which is normally biased into a lock position by a spring. Each function module 804 comprises a corresponding locking recess 1062 configured to retain the hook 910 when in the lock position. The protruding hook has an angled profile which interacts with an edge 1063 of the recess to force the sliding lock into an open position as the function module 804 is manually forced closer to the body mounting module 802. When the function module and body mounting module are fully in contact, the hook protrusion 910 is sufficiently inside the locking recess of the function module so as to allow movement of the sliding lock into the lock position in order to securely fasten the function module to the body mounting module.

Figure 10A:
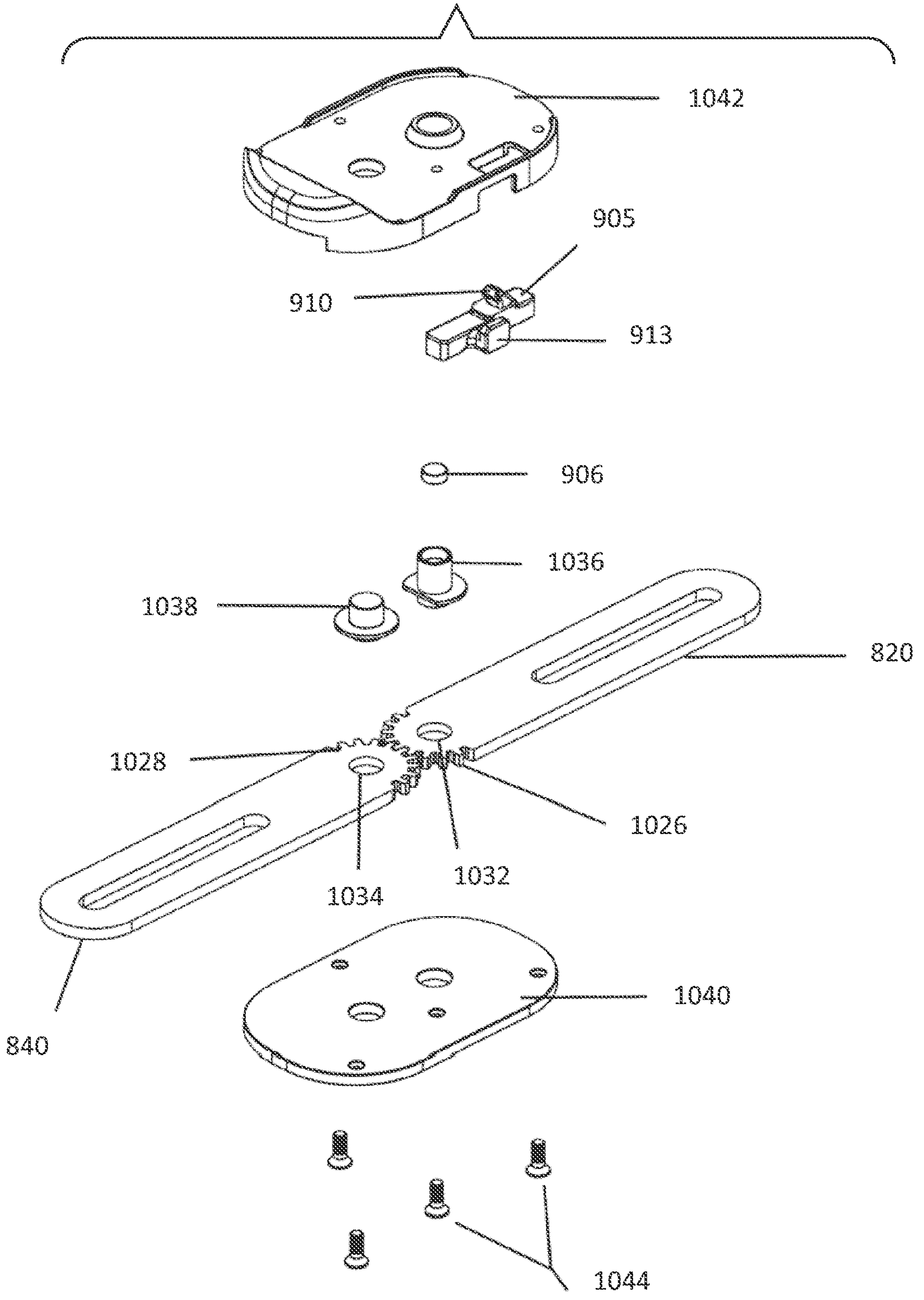
FIG. 10A is an exploded view of a body mounting module of the orthosis system of FIG. 8A.
Figure 10B:
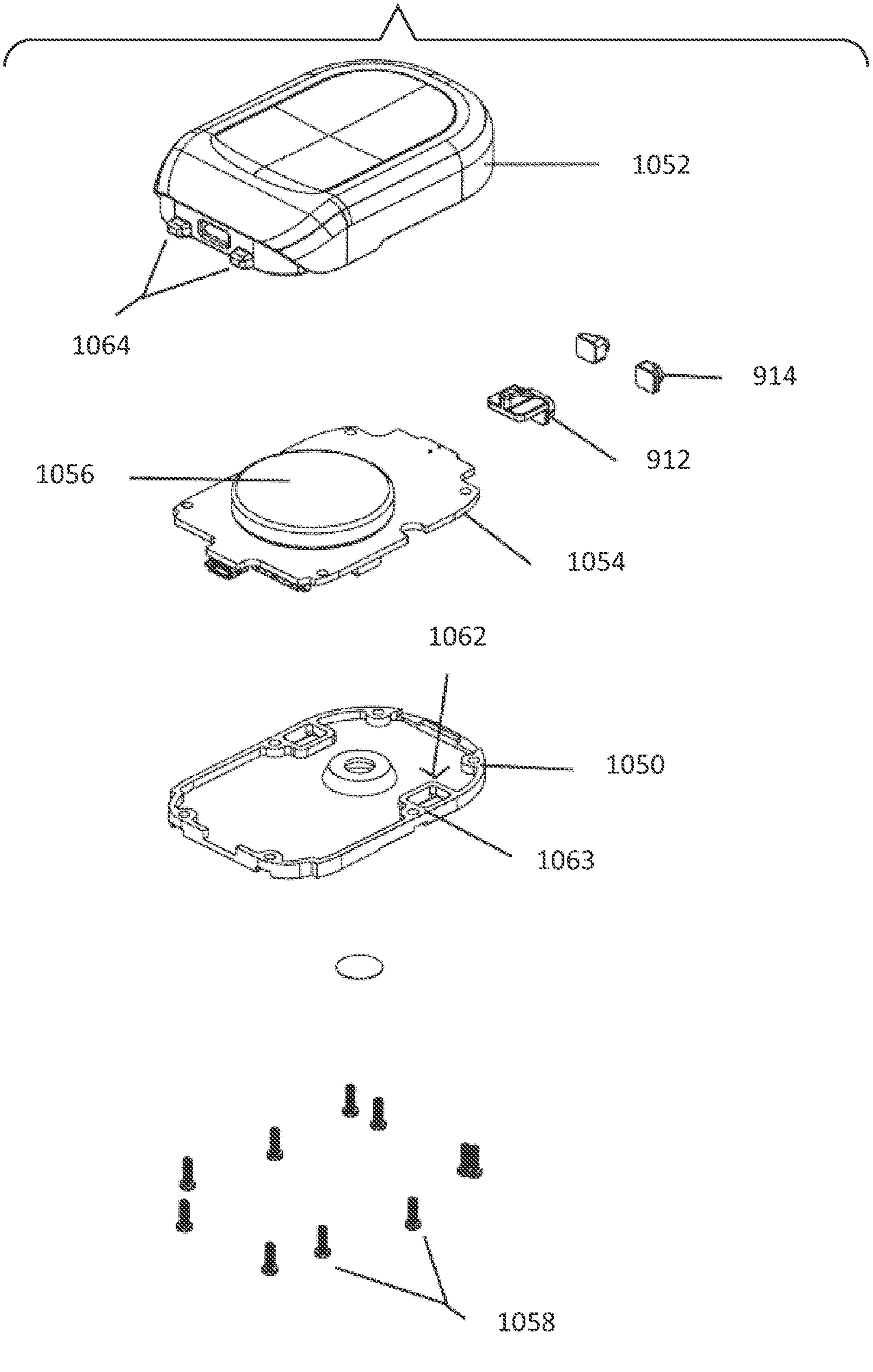
FIG. 10B is an exploded view of a function module of the orthosis system of FIG. 8A.

The locking recess 1062 may comprises be a simple rectangular orifice as shown in FIG. 10B, having an edge 1063 with a thickness corresponding to the hook thickness and to allow the hook to slide inside the recess when fully inside the edge. The sliding lock mechanism and projecting hook are shown in locked position in FIG. 11.

The first and second brace assemblies 820 and 840 comprise respective elongate slots 916 which may be used for attaching the body mounting module 802 to the thigh and shank of a patient using straps as will be described in more detail below. The brace assemblies are polycentrically coupled to each other such that they each rotate about different pivot points. Respective slots 922 and 924 in the body mounting module 802 allow for this movement of the brace assemblies. The brace assemblies may be formed from a structurally rigid material such as metal, alloy or a rigid plastics material, or a combination of materials.

The function modules may comprise one or more control buttons 912, 914 in order to power them on or off, or otherwise control their mode of operation.

The perspective view of FIG. 9 also shows a magnet 906 which rotates with the first brace assembly 820 about its pivot point. The magnet 906 may have its North and South poles aligned in such a way that a magnetic sensor on the function module can be used determine its rotational angle.

FIGS. 10A and 10B respectively show an exploded view of the components of a body mounting module 802 and a function module 804 in more detail. The body mounting module 802 comprises a base plate 1040 and housing 1042 which in use are secured together with screws or bolts 1044. In use the housing contains two ends of the frame assemblies 820 and 840, which ends comprise gear teeth 1026, 1028 positioned to engage each other. Each frame assembly 820, 840 comprises a pivot orifice 1032, 1034 secured at corresponding pivot points on the base plate 1040 and housing 1042 by a respective pivot member 1036, 1038. Together these components are arranged into a polycentric hinge, where the gear teeth engagement ensures that as one of the frame assemblies 820, 840 is rotated about its pivot member 1036, 1038, the other frame assembly 840, 820 is forced to rotate about its respective pivot member 1038, 1036 by an equal angle but in the opposite direction, thereby providing a 1:1 gear ratio. Alternative arrangements may utilise different gear ratios.

The sliding lock mechanism 905 comprises an elongate member which is slide-able within a corresponding recess within the housing 1042. The sliding lock mechanism comprises a hook projection 910 which in use protrudes through an orifice in the housing to engage with a function module. A control surface 913 protrudes through an orifice to the side of the housing to form a button that can be manually engaged by a user to move the sliding lock mechanism 905 within the housing recess.

The function module comprises a base plate 1050, a housing 1052, and a circuit board 1054 onto which is mounted a Hall Effect sensor 1056. The control buttons 912, 914 are retained in position by the housing to engage with active components on the circuit board, for example electrical contacts. The base plate 1050 and housing 1052 are secured together with screws or bolts 1058 to house the circuit board 1054.

The housing 1052 comprises locating and securing projections 1064 which engage with corresponding locating and securing recesses 908 in the housing 1042 of the mounting module 802. The base plate also comprises a locking recess 1062 arranged to cooperate with the hook 910 of the sliding lock 905 in a body mounting module.

Together the securing projections 1064 and locking recess 1062 form the interfacing structure of the function module 804 of this embodiment. Similarly, the locating means 908 and sliding lock mechanism 905 form the interfacing structure of the body mounting module 802 of this module.

The simple “one-click” removal from or coupling to action of the coupling interface allows for a one-handed quick function module replacement.

Figure 11:
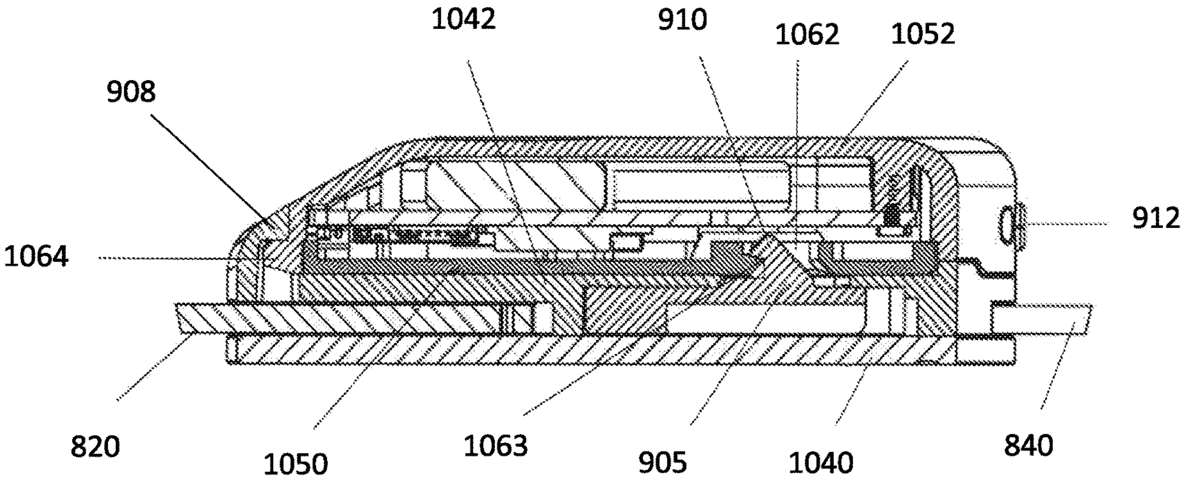
FIG. 11 is a detailed view of the body mounting module of FIG. 10A and the function module of FIG. 10B when coupled.

FIG. 11 is a cross-section of a body mounting module and a function module coupled together. Cooperation of the various component parts previously described can be seen in more detail. The coupling interface of the body mounting module comprises the hook projection 910 on the sliding lock mechanism 905 together with the recesses 908. The coupling interface of the function module comprises the recess 1062 for accepting and retaining the hook 910 together with the projections 1064 which are accepted and retained by the recesses 1064 in the body mounting module. When coupled together the base plate 1050 of the function module rests on the housing 1042 of the body mounting module.

In use, when the body mounting module and the function modules are coupled together, the Hall Effect sensor 1056 is located adjacent the magnet 906 of the coupled body mounting module in order to detect rotational angle changes of the magnet. The signals from the Hall Effect sensor are processed by circuitry on the circuit board 1054 to determine an angle between the first and second frame assemblies, knowing that the frame assemblies are rotational coupled to each other at a 1:1 ratio.

As previously described, the function modules 804 may include different functions such as sensing and recording or transmitting the angle between the thigh and shank when the body mounting module is configured and attached as a knee brace. The body mounting module may be fitted with EMG (electromyography) sensors located adjacent predetermined muscles in order to monitor muscle activity. These sensors may be power and/or monitored by a function module 804, which may also record and/or transmit this information, for example using Bluetooth™, WiFi™ or other communications technologies. In this embodiment the body mounting module and function module will additionally comprise an electrical interface to conduct signals and/or power transfer. Simple electrical contacts may be used, or alternatively pin and socket arrangements. Various alternative electrical interfaces will be appreciated by the skilled person.

The function module 804 may comprise a power sources such as a battery to power sensor or actuator electronics located in the body mounting module, for example a knee angle sensor arrangement. In another example the function module may power electrodes mounted on the body mounting module to stimulate muscle activity, or to power a heating pad. In another implementation, the function module may provide a selectable level of movement to resistance of the brace assemblies. This may be implemented using a magnetic brake mechanism in the function module which interacts with the magnet 906 of the body mounting module. Alternatively, a further mechanical interface may be introduced between the function module and the body mounting module in order to transfer an actuating force, such as a resistance to movement. The mechanical interface may comprise an engagement of gear wheels, or a friction brake applied from the function module to a moveable part of the body mounting module. Other implementations are possible including a clutch, elastomer elements or springs. The function modules with an actuator or control function may have different gear ratios for different functions, for example for in-home/clinic strength exercises, or small lightweight for assistance during walking.

Figure 12:
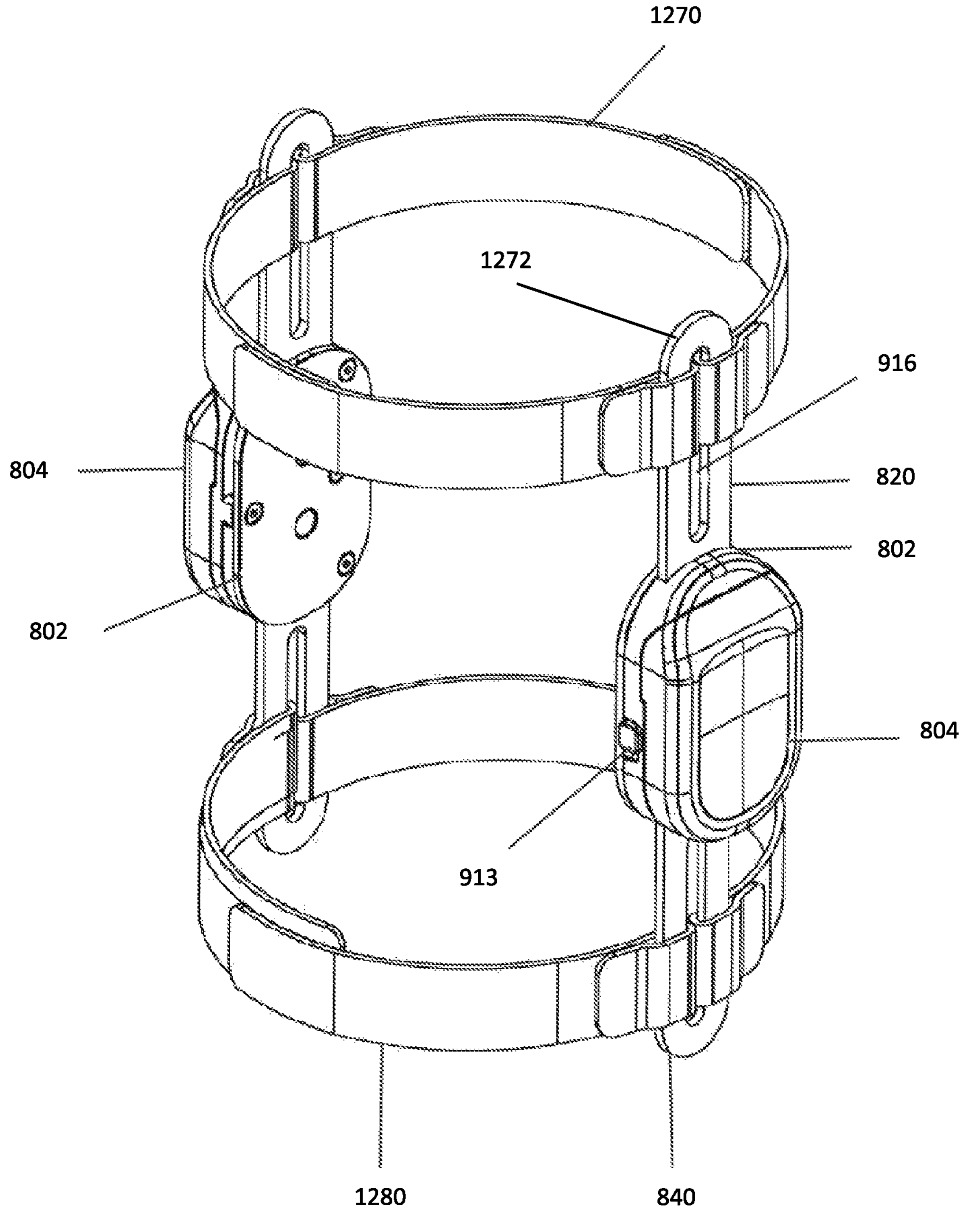
FIG. 12 is an assembled orthosis system according to an embodiment of the present invention.

FIG. 12 shows an assembly of two body mounting modules 802 with distal ends of their two brace assemblies 820 and 840 securable to a patient's leg using straps 1270 and 1280 respectively. The straps may comprise a resilient yet soft material such as a Lycra knitted elastic, Nylon, webbing, open loop Velcro™, foam laminate; and may be secured to the brace assemblies using Velcro™ or any suitable securing mechanism.

The manual release button 913 can be seen on the side of a body mounting module. As previously described, manual actuation of this button causes the slidable locking mechanism 905 to release the hook 910 from the recess 1062 in the function module thereby allowing it to be removed.

Advantages

In providing a modular orthosis system where the control/sensing or function modules are removably couplable to the body mounting module, the present invention offers a system that may be easily modified to suit a patient's rehabilitative needs throughout their recovery. The control/sensing modules may be removed and replaced as required, for instance to record physiological data relating to the patient and subsequently provide resistance and/or limit the patient's range of movement as indicated by the collected data. Alternatively or additionally, the body mounting modules may be removed and replaced as required, for instance a smaller body mounting module may be used once the patient mobility has improved to a certain level, or a body mounting module having a different configuration may be used for a new phase in the patient's rehabilitation. The same control/sensing module may be coupled to the new body mounting module.

This may provide a versatile and economical solution. The patient may be monitored remotely using the system and may implement a specialist's instructions by coupling an appropriate control/sensing module to an appropriate body mounting module and configuring both as required. This may result in fewer visits to specialists, and/or it may avoid the need to change the entire brace including specialised sensor/control functionality when the patient's rehabilitative requirements change.

The control/sensing or function modules are straightforward to connect and remove while also affording robust connection to a body mounting module. The use of tools is not required to effect connection of the control/sensing modules to the body mounting modules. Furthermore, the simplicity of the coupling systems may enable the patient to connect the control/sensing modules with one hand. The modules can be interchanged easily and quickly depending on the functional requirement required. The functional requirement can be the choice of the wearer or may also be prescribed by a trained clinician or via a notification on a user interface (such as mobile or web interface).

A further advantage of the present invention is that its modularity means that forces encountered by the system are borne by the relatively robust body mounting modules, and are substantially not transferred to the control/sensing modules, which are fixedly coupled to and therefore able to move with the bracing assemblies rather than absorbing applied forces. This may help to protect the control/sensing modules from damage, providing a relatively more robust and durable system.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. An orthosis or exoskeleton system comprising:

two or more body mounting modules and one or more function modules;

the or each body mounting module of the one or more body mounting modules being structured and arranged to, in use, be mounted to respective first and second body parts of a patient, the first and second body parts being either side of a joint of the patient; and the or each function module of the two or more function modules being structured and arranged to provide a sensing function;

the or each body mounting module of the one or more body mounting modules and the or each function module of the two or more function modules each having an interfacing structure such that any of said one or more body mounting modules is interchangeably couplable to any of said two or more function modules, wherein the one or more body mounting modules and the two or more function modules each have a transfer interface such that information may be transferred between one respective body mounting module and one respective function module when coupled, wherein the one or more body mounting modules comprises first and second brace assemblies, the first brace assembly pivotably coupled to the second brace assembly using a hinge; wherein the transfer interface includes a magnet arranged to rotate with the first brace assembly and a Hall Effect sensor arranged on the one respective function module to detect the rotation of the magnet, wherein the sensing function is dependent on an angle between the first and second body part.

2. A system according to claim 1, wherein the interfacing structures are configured to provide a quick release or tool-less coupling between the one respective body mounting module of the one or more body mounting modules and the one respective function module of the two or more function modules.

3. A system according to claim 1, wherein one body mounting module of the one or more body mounting modules is further structured and arranged to provide a control function, and one of the two or more function modules is further structured and arranged to provide a power source to power sensor or control electronics located in said body mounting module and is structured and arranged to provide a charging function to charge the power source.

4. A system according to claim 1, wherein the information is selected from one of the following: an angle between different parts of the body mounting module; an orientation of the body mounting module or function module; movement of the body mounting module or function module; muscle activity of a body part of the patient; patient proximity; body temperature; heart rate; respiration rate; blood pressure; blood oxygen level; joint/body forces and/or load.

5. A system according to claim 1, wherein the first brace assembly is pivotably coupled to the second brace assembly using a unicentric hinge.

6. A system according to claim 1, wherein the first and second brace assemblies each comprise first and second brace interfacing structures respectively forming the interfacing structure of the one or more of the body mounting modules, each of the two or more function modules comprising a complementary interfacing structure which is arranged to engage with one of the first or the second brace interfacing structures when the two or more function modules are coupled to the one or more body mounting modules.

7. A system according to claim 1, wherein the first and second brace assemblies each comprise first and second pivot portions respectively, the first and second pivot portions being pivotably coupled at a pivot assembly, the pivot assembly being configured to couple to the two or more function modules.

8. A system according to claim 1, wherein the interfacing structure of the two or more functional modules and the first brace interfacing structure comprise a first locking mechanism to lock the orientation of the two or more function modules relative to the first brace assembly.

9. A system according to claim 1, wherein the two or more function modules comprises a rotation limitation mechanism configured to limit rotation of the first brace assembly relative to the second brace assembly.

10. A system according to claim 1, wherein the two or more function modules comprises a resistance mechanism configured to provide a predetermined level of resistance to rotation of the first brace assembly relative to the second brace assembly.

11. A system according to claim 1, wherein the pivot assembly is configured to couple to the two or more function modules by rotating the two or more function modules relative to the pivot assembly.

12. A system according to claim 1, wherein the interfacing structure of the one or more body mounting modules comprises a slide-able lock mechanism and the interface of the two or more function modules comprises a locking recess which is arranged to engage with the slide-able lock mechanism to couple the one or more body mounting modules to the two or more function modules.

13. A system according to claim 1, wherein the interfacing structure of the one or more body mounting modules comprises a number of locating recesses and the interfacing structure of the two or more function modules comprises a number of locating projections which are arranged to engage with the locating recesses to couple the one or more body mounting modules to the two or more function modules.

* * * * *